US007686765B2

(12) United States Patent
Nakamura et al.

(10) Patent No.: US 7,686,765 B2
(45) Date of Patent: Mar. 30, 2010

(54) PULSE DETECTING DEVICE AND ULTRASOUND DIAGNOSTIC APPARATUS

(75) Inventors: Takahiko Nakamura, Chiba (JP);
Masataka Shinogi, Chiba (JP);
Hiroyuki Muramatsu, Chiba (JP);
Hiroshi Odagiri, Chiba (JP)

(73) Assignee: Seiko Instruments Inc. (JP)

( * ) Notice: Subject to any disclaimer, the term of this patent is extended or adjusted under 35 U.S.C. 154(b) by 1210 days.

(21) Appl. No.: 11/096,876

(22) Filed: Apr. 1, 2005

(65) Prior Publication Data
US 2005/0203403 A1    Sep. 15, 2005

Related U.S. Application Data

(62) Division of application No. 10/460,005, filed on Jun. 12, 2003, now Pat. No. 6,887,205, which is a division of application No. 09/893,392, filed on Jun. 28, 2001, now abandoned.

(30) Foreign Application Priority Data

| Jul. 12, 2000 | (JP) | ............................. 2000-211213 |
| Jul. 12, 2000 | (JP) | ............................. 2000-211214 |
| Feb. 7, 2001 | (JP) | ............................. 2001-030996 |

(51) Int. Cl.
*A61B 8/00* (2006.01)

(52) U.S. Cl. ....................... 600/459; 600/437; 600/439; 600/461; 600/462; 367/117; 367/118

(58) Field of Classification Search .................. 600/459, 600/437, 461, 462; 367/117, 118
See application file for complete search history.

(56) References Cited

U.S. PATENT DOCUMENTS

| 4,086,916 | A | * | 5/1978 | Freeman et al. ............. 600/453 |
| 4,651,310 | A | * | 3/1987 | Kaneko et al. ............. 367/140 |
| 5,176,140 | A | * | 1/1993 | Kami et al. ................. 600/459 |
| 5,680,863 | A | * | 10/1997 | Hossack et al. ............. 600/459 |
| 6,091,406 | A | * | 7/2000 | Kambara et al. ............ 345/177 |
| 6,295,247 | B1 | * | 9/2001 | Khuri-Yakub et al. ....... 367/140 |
| 6,314,057 | B1 | * | 11/2001 | Solomon et al. ............ 367/174 |
| 6,328,696 | B1 | * | 12/2001 | Fraser ......................... 600/459 |
| 6,394,960 | B1 | * | 5/2002 | Shinogi et al. .............. 600/503 |
| 6,447,456 | B1 | * | 9/2002 | Tsubata ..................... 600/455 |

(Continued)

FOREIGN PATENT DOCUMENTS

EP          186096     A    *    7/1986

*Primary Examiner*—Brian Casler
*Assistant Examiner*—Baisakhi Roy
(74) *Attorney, Agent, or Firm*—Adams & Wilks

(57) ABSTRACT

There is provided a pulse detecting device which resists fluctuations in the quality by locating an ultrasound transmitting piezoelectric element and an ultrasound receiving piezoelectric element with high precision. In the pulse detecting device, a detection sensitivity of the pulse is improved. A transmitting piezoelectric element and a receiving piezoelectric element are fixed onto a substrate by electrodes. The transmitting piezoelectric element is excited in response to an inputted drive voltage signal to generate an ultrasound and transmits the generated ultrasound to a living body. The receiving piezoelectric element receives an echo produced by reflecting the ultrasound transmitted into the living body by a blood flow of the living body and converts it into a voltage signal. A processing arithmetic unit compares the frequency of the ultrasound generated by the transmitting piezoelectric element with that of the echo received in the receiving piezoelectric element to thereby detect a pulse.

17 Claims, 15 Drawing Sheets

U.S. PATENT DOCUMENTS 6,554,772 B2 * 4/2003 Nakamura et al. .......... 600/459
6,783,495 B2 * 8/2004 Ogawa ....................... 600/437
2001/0031922 A1 * 10/2001 Weng et al. ................. 600/439
2007/0035201 A1 * 2/2007 Desilets et al. .............. 310/311

* cited by examiner

PULSE DETECTING DEVICE AND ULTRASOUND DIAGNOSTIC APPARATUS

This application is a division of application Ser. No. 10/460,005 filed Jun. 12, 2003 and now U.S. Pat. No. 6,887,205, which is a division of application Ser. No. 09/893,392 filed Jun. 28, 2001 and now abandoned.

BACKGROUND OF THE INVENTION

1. Field of the Invention

The present invention relates to a pulse detecting device using a piezoelectric element as a detection element and an ultrasound diagnostic apparatus using the piezoelectric element.

2. Description of the Related Art

Important information that can be applied to the diagnostic of a disease is included in the pulse of a living body. Thus, recently, the following system is studied in a medical facility such as a hospital. That is, in this system, a portable type pulse detecting device is put on a patient's wrist, and then pulse detection data of the patient that is transmitted from this portable type pulse detecting device is received in a hospital to evaluate a state of the patient. It is effective to use the piezoelectric element for miniaturization and weight reduction of the pulse detecting device. Thus, based on the application to the above system, the development of the pulse detecting device using the piezoelectric element has progressed. In addition, an ultrasound diagnostic apparatus for obtaining information of a living body or an object using ultrasound is well known. This ultrasound diagnostic apparatus irradiates (transmits) an ultrasound into a diagnostic portion of a person to be examined or a diagnostic object, detects an echo produced by reflecting the ultrasound by the diagnostic portion, and obtains information with respect to the diagnostic portion in accordance with this detection result.

A conventional pulse detecting device 100 using the piezoelectric element is shown in FIG. 32. As shown in the drawing, in the pulse detecting device 100, two piezoelectric elements 110 and 120 are embedded in resin (or gel) 130 and fixed therein. Here, metal electrodes (not shown) are formed on both surfaces of the respective piezoelectric elements 110 and 120 in a thickness direction. Also, although not shown, drive voltage applying probes (terminals, lead wirings and the like) are connected with both electrodes of the piezoelectric element 110 and voltage signal outputting probes (terminals, lead wirings and the like) are connected with both electrodes of the piezoelectric element 120.

Also, for example, a pulse detecting device using an ultrasound transmits the ultrasound to the radial artery of a person to be examined and obtains a waveform of a pulse wave and a pulse rate from changes in a amplitude and a frequency of an echo.

Then, at an examination in a hospital, the pulse detecting device 100 is used to detect the pulse of a patient. With respect to details, when the drive voltage is applied to both electrodes of the piezoelectric element 110, the piezoelectric element 110 is excited to generate the ultrasound. The generated ultrasound is transmitted into a living body through the resin 130. The ultrasound transmitted into the living body is reflected by a blood flow of the living body and the reflected ultrasound is received in the piezoelectric element 120 through the resin 130. At this time, a change in a frequency due to a Doppler effect of the blood flow is produced between the ultrasound transmitted from the piezoelectric element 110 and the ultrasound received in the piezoelectric element 120. In addition, since the velocity of the blood flow is changed in synchronization with the pulse, the pulse of the living body is detected from the change in the frequency of the ultrasound.

Now, in the above pulse detecting device using the piezoelectric element, in order to improve the receiving sensitivity of ultrasound, it is necessary to locate the piezoelectric element 110 for transmitting the ultrasound and the piezoelectric element 120 for receiving the ultrasound with high precision.

The above pulse detecting device 100 is manufactured by arranging two piezoelectric elements 110 and 120 in predetermined positions of a mold and then pouring the resin 130 into the mold. However, When the resin 130 is poured into the mold, there is a possibility that positions and location angles of these piezoelectric elements are shifted, and thus there is a problem that a high precision arrangement of the piezoelectric elements is difficult.

Therefore, there is a possibility that the quality of the conventional pulse detecting device 100 is varied.

Also, generally, in the pulse detecting device using the piezoelectric element, in order to improve the receiving sensitivity of ultrasound, it is necessary to locate the ultrasound transmitting piezoelectric element and the ultrasound receiving piezoelectric element with high precision. Also, if the ultrasound is propagated through the inner portion of a substrate and then directly received in the ultrasound receiving piezoelectric element, this causes a noise and further strengths of a transmitting wave and a receiving wave to the blood flow, which are required for measuring the pulse are decreased. As a result, the detection sensitivity of the pulse is reduced. Therefore, in order to improve the detection sensitivity of the pulse, it is necessary to make a structure in which the ultrasound does not easily propagate through the inner portion of the substrate and then directly received in the ultrasound receiving piezoelectric element. Further, as the resin 130 becomes thicker, the strength of the ultrasound transmitted to the blood flow in the living body is decreased.

However, the above pulse detecting device 100 is manufactured by arranging two piezoelectric elements 110 and 120 in predetermined positions of a mold and then pouring the resin 130 into the mold. Accordingly, there are the following problems.

(1) When the resin is poured into the mold, there is a possibility that positions and location angles of these piezoelectric elements are shifted, and thus there is a problem that a high precision arrangement of the piezoelectric elements is difficult. Therefore, there is a possibility that the quality is varied.

(2) Since the pulse detecting device has a structure that the ultrasound is directly and easily received in the receiving piezoelectric element through the resin, there is a limitation in the detection sensitivity of the pulse.

(3) Since it is difficult to manufacture the resin 130 thin, there is a limitation in the detection sensitivity of the pulse.

Also, with respect to the ultrasound diagnostic apparatus, there are the same problems as in the pulse detecting device as described above.

SUMMARY OF THE INVENTION

Thus, an object of the present invention is to provide a pulse detecting device which resists fluctuations in the quality by locating an ultrasound transmitting piezoelectric element and an ultrasound receiving piezoelectric element with high precision and a method of manufacturing the same. In addition, an object of the present invention is to improve the detection sensitivity of the pulse in the pulse detecting device.

Also, another object of the present invention is to provide a pulse detecting device which resists fluctuations in the quality and a pulse detecting device having a structure for improved sensitivity, by arranging the ultrasound transmitting piezoelectric element and the ultrasound receiving piezoelectric element with high precision.

Also, another object of the present invention is to provide an ultrasound diagnostic apparatus which resists fluctuations in the quality, an ultrasound diagnostic apparatus having a structure for improved sensitivity, and a method of manufacturing such an ultrasound diagnostic apparatus, by arranging the ultrasound transmitting piezoelectric element and the ultrasound receiving piezoelectric element with high precision.

To solve the above problems, a pulse detecting device according to the present invention is constructed such that at least one of a transmitting piezoelectric element (piezoelectric element for transmitting an ultrasound into a living body in response to an inputted drive signal) and a receiving piezoelectric element (piezoelectric element for receiving an echo produced by reflecting the ultrasound by a blood flow of the living body) is fixed onto the substrate through the feed portion for applying the drive signal to the transmitting piezoelectric element. According to this structure, since at least one of the transmitting piezoelectric element and the receiving piezoelectric element is located and fixed onto the substrate, those piezoelectric elements can be located with high precision as designed.

Therefore, according to the structure of the present invention, the pulse detecting device which resists fluctuations in the quality can be provided. In addition, since the piezoelectric elements are fixed onto the substrate in the feed portion rather than onto the entire surface of the substrate, the ultrasound does not easily propagate to the substrate and the noise can be decreased. In addition, the sensitivity can be improved.

A gap is produced between the substrate and the piezoelectric elements. According to such a structure, the ultrasound does not easily propagate from the transmitting piezoelectric element to the substrate and the possibility that the ultrasound is propagated into the substrate and directly received in the receiving piezoelectric element becomes lower. Thus, the noise can be decreased. In addition, the sensitivity can be improved.

A structure in which the feed portion protrudes to the piezoelectric elements, a structure in which the piezoelectric elements protrude toward the feed portion, or a substrate made of a porous material is used. Therefore, the structure is obtained so as to further lower the possibility that the ultrasound is propagated into the substrate and directly received in the receiving piezoelectric element. Thus, the noise can be decreased. In addition, the sensitivity can be improved.

A structure is used such that a groove is provided in a portion of the substrate and the transmitting piezoelectric element and the receiving piezoelectric element are located sandwiching the groove. According to this structure, the ultrasound generated by the transmitting piezoelectric element is reflected and attenuated by the groove between the transmitting piezoelectric element and the receiving piezoelectric element. Thus, the possibility that the ultrasound is propagated into the substrate and directly received in the receiving piezoelectric element becomes further low. Therefore, the sensitivity of the pulse detecting device can be improved.

Alternatively, the substrate may be divided into two division substrates, the transmitting piezoelectric element may be located on one of the division substrates, and the receiving piezoelectric element may be located on the other division substrate. In this case, it becomes even more unlikely that the ultrasound generated by the transmitting piezoelectric element directly propagates to the receiving piezoelectric element. Thus, the sensitivity of the pulse detecting device can be improved.

A structure is used such that a resin layer is provided on a piezoelectric element locating surface of the substrate to effectively transmit the ultrasound into the living body. Since the piezoelectric elements are located on the substrate, the resin layer can be easily located with a constant thickness. Also, a structure is used such that the resin layer is divided between the transmitting piezoelectric element and the receiving piezoelectric element and thus it is unlikely that the ultrasound generated by the transmitting piezoelectric element directly propagates to the receiving piezoelectric element through the resin layer.

A support substrate is provided. Thus, the strength against an external shock and the ease of handling of the pulse detecting device is improved.

A structure having a display unit for displaying a pulse detected by a detection unit may be used. When a structure having a belt for putting the pulse detecting device on the wrist is used, the living body can easily carry the pulse detecting device.

To solve the above problems, a pulse detecting device according to the present invention includes: a transmitting and receiving substrate in which a transmitting piezoelectric element and a receiving piezoelectric element are fixed and located on one surface and the other surface is in contact with a living body; and a support for supporting the transmitting and receiving substrate, which is not in contact with the transmitting piezoelectric element and the receiving piezoelectric element. According to such a structure, both the transmitting piezoelectric element and the receiving piezoelectric element are fixed and located on the transmitting and receiving substrate. Thus, these piezoelectric elements can be located on the substrate with high precision as designed. In addition, the ultrasound generated by the transmitting piezoelectric element is transmitted to the living body through the transmitting and receiving substrate, and the echo produced by reflecting the ultrasound by the blood flow of the living body is propagated from the living body to the receiving piezoelectric element through the transmitting and receiving substrate. Thus, there is no problem in the operation.

The transmitting piezoelectric element oscillates in all directions when placed in the inside of resin. However, since a space is present in a rear side of the transmitting piezoelectric element, the oscillation is propagated to only the substrate side without a waste. Thus, according to the structure of the present invention, a pulse detecting device which resists fluctuations in the quality can be provided. In addition, the detection sensitivity of the pulse can be improved.

An acoustic impedance of the transmitting and receiving substrate is set to be a value between that of respective piezoelectric elements and that of the living body. Therefore, when the acoustic impedance of the transmitting and receiving substrate is set to be such a value, the ultrasound generated by the transmitting piezoelectric element can be transmitted to the living body with high efficiency without reflecting it by an interface between the transmitting and receiving substrate and the living body. In addition, the echo due to the pulse of the living body can be received in the receiving piezoelectric element with high sensitivity without reflecting it by the interface.

The thickness of the transmitting and receiving substrate is set to be about a quarter of a wavelength of the ultrasound generated by the transmitting piezoelectric element. Therefore, the reflection of the ultrasound by the interface between the substrate and the living body can be reduced, and thus the ultrasound is transmitted into the living body with high efficiency. In addition, the echo can be received in the receiving piezoelectric element with high sensitivity.

A structure is used such that a resin layer is provided on a surface that is in contact with the living body. By providing the resin layer, a property of the surface in contact with the living body can be suitably adjusted dependent on its use. For example, when a silicon based resin is used for the resin layer, the adhesiveness between the transmitting and receiving substrate and the living body is improved. Therefore, since an amount of air entering the interface between the transmitting and receiving substrate and the living body is decreased, an attenuation of oscillation of the ultrasound becomes less and thus the ultrasound can be propagated with high efficiency. In addition, silicon based resin has high compatibility with the living body. Thus, even if this resin is in close contact with the skin, the influence to the skin is small.

The transmitting and receiving substrate may be divided into two division substrates, the transmitting piezoelectric element may be located on one of the division substrates, and the receiving piezoelectric element may be located on the other division substrate in this case, the ultrasound generated by the transmitting piezoelectric element is not directly propagated to the receiving piezoelectric element. Thus, the noise can be decreased and the reliability of the pulse detecting device can be improved.

The transmitting and receiving substrate is formed to slant one surface against the other surface. For example, one surface of the transmitting and receiving substrate is not in parallel with the other surface thereof and the transmitting and receiving substrate is formed with the taper shape. Therefore, the Doppler effect of the blood flow becomes larger. Also, a change in a frequency between the ultrasound generated by the transmitting piezoelectric element and the echo received in the receiving piezoelectric element becomes larger. Thus, the detection sensitivity of the pulse in the pulse detecting device is improved.

A support for supporting the transmitting piezoelectric element and the receiving piezoelectric element, which are located on the transmitting and receiving substrate, is used. Thus, the strength of the pulse detecting device against an external shock and the durability thereof is improved.

A structure having a display unit for displaying a pulse detected by a detection unit may be used. When a structure having a belt for putting the pulse detecting device on the wrist is used, the living body can easily carry the pulse detecting device.

Further, to solve the above problems, a pulse detecting device according to the present invention includes: a piezoelectric element for transmitting an ultrasound into a living body in response to an inputted drive signal (hereinafter referred to as a transmitting piezoelectric element); a piezoelectric element for receiving an echo produced by reflecting the ultrasound by a diagnostic portion of the living body (hereinafter referred to as a receiving piezoelectric element); a substrate for fixing the transmitting-piezoelectric element and the receiving piezoelectric element onto one surface; a detection unit for detecting information with respect to the diagnostic portion from the ultrasound generated by the transmitting piezoelectric element and the echo; and a feed portion for applying the drive signal to the transmitting piezoelectric element provided on the substrate, the substrate and the piezoelectric element being fixed in the feed portion on the substrate.

According to this structure, since both the transmitting piezoelectric element and the receiving piezoelectric element are fixed and located on the substrate, these piezoelectric elements can be located with high precision as designed. Therefore, according to the structure of the present invention, the pulse detecting device which resists fluctuations in the quality can be provided. Also, since the piezoelectric elements are fixed onto the substrate in the feed portion rather than onto the entire surface of the substrate, the ultrasound does not easily propagate to the substrate and the noise can be decreased. In addition, the sensitivity can be improved.

A structure is used such that a gap is produced between the substrate and the piezoelectric elements. According to this structure, the ultrasound does not easily propagate from the transmitting piezoelectric element to the substrate and the possibility that the ultrasound is propagated into the substrate and directly received in the receiving piezoelectric element becomes lower. Thus, the noise can be decreased. In addition, the sensitivity can be improved.

A structure in which the feed portion protrudes to the piezoelectric elements, a structure in which the piezoelectric elements protrude toward the feed portion, or a substrate made of a porous material is used. Therefore, the structure is obtained so as to further lower the possibility that the ultrasound is propagated into the substrate and directly received in the receiving piezoelectric element. Thus, the noise can be decreased. In addition, the sensitivity can be improved.

A structure is used such that a groove is provided in a portion of the substrate and the transmitting piezoelectric element and the receiving piezoelectric element are located sandwiching the groove. According to this structure, the ultrasound generated by the transmitting piezoelectric element is reflected and attenuated by the groove between the transmitting piezoelectric element and the receiving piezoelectric element on the substrate. Thus, the possibility that the ultrasound is propagated into the substrate and directly received in the receiving piezoelectric element becomes further low. Therefore, the detection sensitivity can be improved.

Alternatively, the substrate may be divided into two division substrates, the transmitting piezoelectric element may be located on one of the division substrates, and the receiving piezoelectric element may be located on the other division substrate. In this case, it is even more unlikely that the ultrasound generated by the transmitting piezoelectric element directly propagates to the receiving piezoelectric element. Thus, the detection sensitivity can be improved.

A structure is used such that a resin layer is provided on a piezoelectric element locating surface of the substrate to effectively transmit the ultrasound into the living body. Since the piezoelectric elements are located on the substrate, the resin layer can be easily located with a constant thickness. Also, a structure is used such that the resin layer is divided between the transmitting piezoelectric element and the receiving piezoelectric element and thus the ultrasound generated by the transmitting piezoelectric element is unlikely to directly propagate to the receiving piezoelectric element through the resin layer.

By providing a support, the strength against an external shock and the ease of handling of the pulse detecting device is improved.

The thickness of the gap is set to be a wavelength ё of the ultrasound or more. Thus, the above attenuation characteristic is improved and the ultrasound generated by the transmitting piezoelectric element is unlikely to directly propagate to the receiving piezoelectric element. Therefore, the detection sensitivity can be improved.

DETAILED DESCRIPTION OF THE PREFERRED EMBODIMENTS

Figure 1:
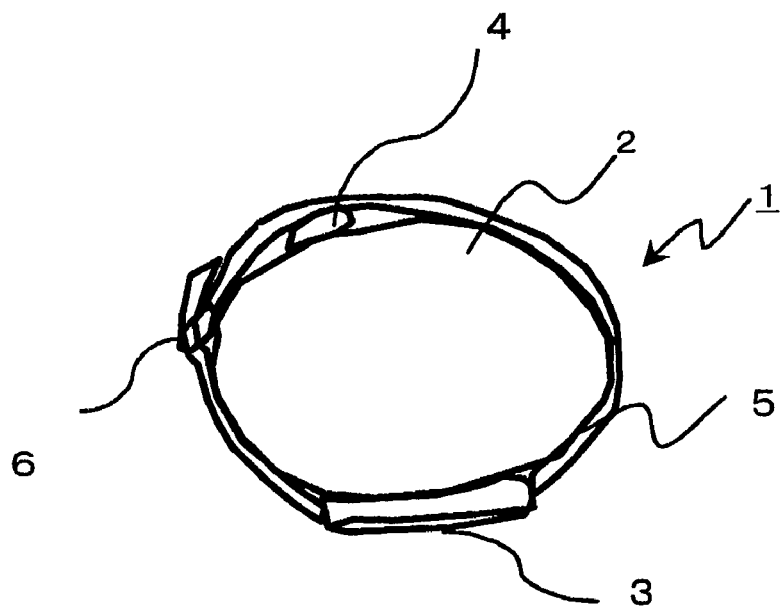
FIG. 1 is an outer appearance view showing a structure of a pulse detecting device to which the present invention is applied.

A pulse detecting device of the present invention includes: a transmitting piezoelectric element for transmitting an ultrasound into a living body in response to an inputted drive signal; a receiving piezoelectric element for receiving an echo produced by reflecting the ultrasound by a blood flow of the living body; a substrate in which these piezoelectric elements are provided on one surface; a detection unit for detecting a pulse from the echo; and a feed portion, provided on the substrate, for applying the drive signal to the transmitting piezoelectric element, the substrate and the transmitting piezoelectric element being fixed onto the substrate in the feeding portion. According to this structure, both the transmitting piezoelectric element and the receiving piezoelectric element are located and fixed onto the substrate. Thus, these piezoelectric elements can be located with high precision as designed.

Since the transmitting piezoelectric element is fixed in only the feed portion required for inputting a drive signal, the oscillation by the transmitting piezoelectric element does not easily propagate to the entire substrate. Thus, the possibility that the ultrasound is propagated into the substrate and directly received in the receiving piezoelectric element becomes lower. Therefore, the noise can be prevented and the detection sensitivity of the pulse can be improved.

When a gap is provided between the substrate and the piezoelectric elements, the possibility that the ultrasound is propagated into the substrate and directly received in the receiving piezoelectric element becomes further low. Thus, the sensitivity can be improved.

When a structure in which the feed portion protrudes toward the piezoelectric elements, a structure in that the piezoelectric elements protrude to the feed portion, or a substrate made of a porous material is used, the structure is obtained so as to lower the possibility that the ultrasound is propagated into the substrate and directly received in the receiving piezoelectric element. Thus, the sensitivity can be improved.

When a support substrate for supporting the substrate is provided, the strength and the ease of handling can be improved. The details will be described in the embodiments hereinbelow.

A pulse detecting device according to the present invention is constructed such that a piezoelectric element for transmitting an ultrasound into a living body in response to an inputted drive electric signal or a piezoelectric element for receiving an echo produced by reflecting the ultrasound by a blood flow of the living body, is provided on a support or one surface of a substrate, and a space is produced in the side opposite to the living body side sandwiching the piezoelectric elements.

According to the pulse detecting device with such a structure, the piezoelectric elements are located and fixed onto the support or the substrate. Thus, these piezoelectric elements can be located with high precision as designed. Therefore, according to the structure of the present invention, fluctuations in the quality are less likely to occur and the detection sensitivity of the pulse can be improved.

An acoustic impedance of the substrate is set to be a value between that of the piezoelectric elements and that of the living body. A thickness of the substrate is set to be about a quarter of a wavelength of the ultrasound generated by the transmitting piezoelectric element. A resin layer is provided on a surface that is in contact with the living body. The details will be described in the following embodiments.

Hereinafter, embodiments of the present invention will be described in details with reference to the drawings.

Embodiment 1

A pulse detecting device according to Embodiment 1 of the present invention will be described in details with reference to FIGS. 1 to 6.

First, an outer appearance of the pulse detecting device 1 will be described with reference to FIGS. 1 and 2.

Figure 2:
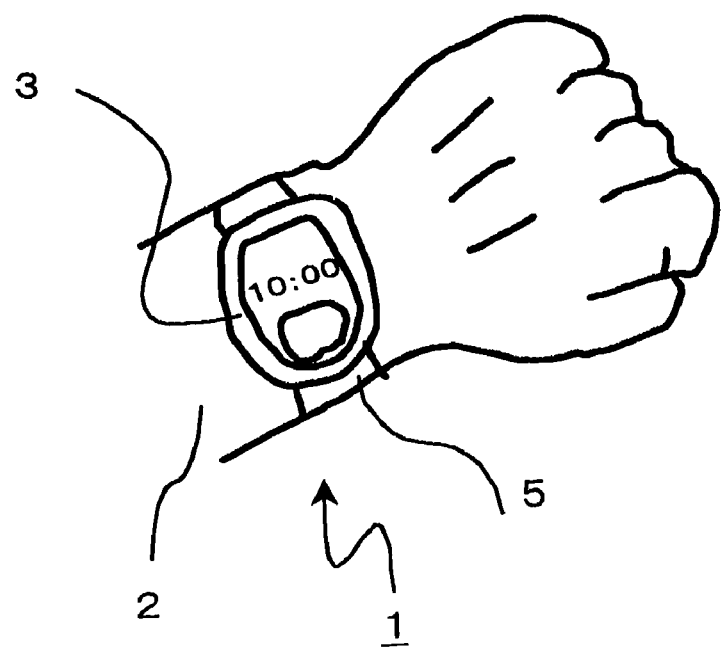
FIG. 2 is an outer appearance view showing a state in which the pulse detecting device of the present invention is put on a living body (wrist)

FIG. 1 is a side view showing a structure in an outer appearance of the pulse detecting device 1 to which the present invention is applied and FIG. 2 shows a state in which the pulse detecting device 1 shown in FIG. 1 is put on a living body (wrist) 2.

As shown in FIG. 1, the pulse detecting device 1 is substantially constructed by a processing unit 3, a measurement unit 4, a band 5, and a clip 6. As shown in FIG. 2, the pulse detecting device 1 is always portable by being put on the living body 2. Here, the processing unit 3 and the measurement unit 4 are attached to the band 5, and thus these are put on the living body 2 (the broken line portion in the drawing) by the band 5 and the clip 6. At this time, the measurement unit 4 is located in contact with a vicinity of the radial artery or the ulnar artery in the living body 2 (not shown). In addition, although not shown, the processing unit 3 and the measurement unit 4 are connected with each other through wirings. A drive voltage signal is inputted from the processing unit 3 to the measurement unit 4 through the wirings. A voltage signal measured by the measurement unit 4 is inputted to the processing unit 3.

Figure 3:
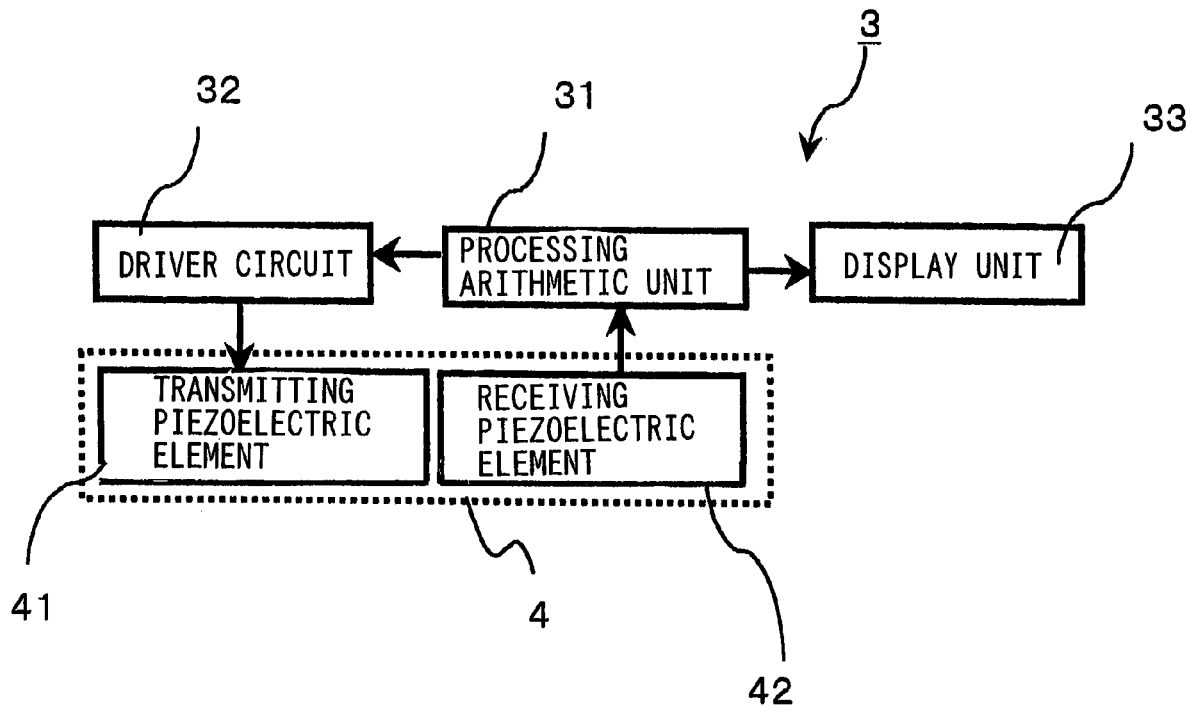
FIG. 3 is a block diagram showing an inner structure of a processing unit and a connection state between the processing unit and a measurement unit.

Next, the processing unit 3 of the pulse detecting device 1 will be described with reference to FIG. 3. FIG. 3 is a block diagram showing an inner structure of the processing unit 3 and a connection state between the processing unit 3 and the measurement unit 4. As shown in FIG. 3, the processing unit 3 is substantially constructed by a processing arithmetic unit 31, a driver circuit 32, and a display unit 33.

The processing arithmetic unit 31 executes a processing program stored in a memory region (not shown) provided in the inner portion to perform various processings with respect to the detection of the pulse and causes the display unit 33 to display a processing result.

The processing arithmetic unit 31 causes the driver circuit 32 to output a specific drive voltage signal to a transmitting piezoelectric element 41 (described later with respect to details) of the measurement unit 4 when the pulse is measured.

Also, the processing arithmetic unit 31 compares the frequency of the ultrasound emitted from the transmitting piezoelectric element 41 with that of the ultrasound that is received in a receiving piezoelectric element 42 and changed due to a Doppler effect of the blood flow, and thus detects the pulse.

The driver circuit 32 outputs a specific drive voltage signal to the transmitting piezoelectric element 41 of the measurement unit 4 in response to instructions of the processing arithmetic unit 31.

The display unit 33 is composed of a liquid crystal display screen and the like and displays a pulse detection result and the like that are inputted from the processing arithmetic unit 31.

Figure 4:
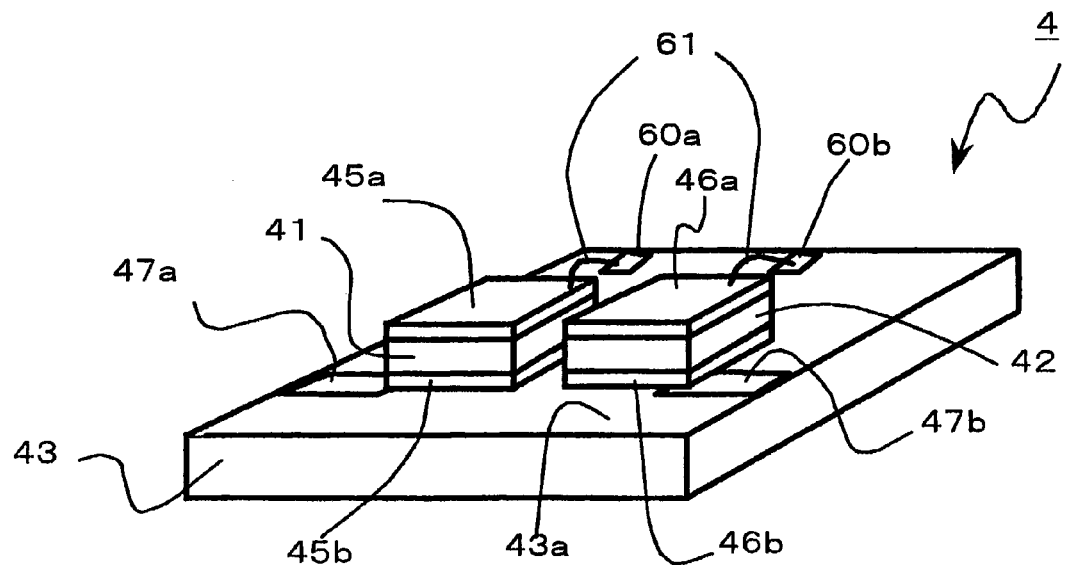
FIG. 4 shows a structure of the measurement unit in the pulse detecting device of the present invention.

Next, the measurement unit 4 of the pulse detecting device 1 will be described with reference to FIGS. 4 and 5. FIG. 4 is a schematic view showing a structure of the measurement unit 4 and FIG. 5 is a top view of the measurement unit 4.

As shown in FIG. 4, the measurement unit 4 is substantially constructed by the transmitting piezoelectric element 41, the receiving piezoelectric element 42, and a substrate 43. Here, electrodes 45a and 45b and electrodes 46a and 46b are formed on both surfaces of the transmitting piezoelectric element 41 and the receiving piezoelectric element 42 in a thickness direction. Also, electrodes 47a and 47b and top electrodes 60a and 60b are formed on one surface 43a of the substrate 43. The electrodes 45a and 46a are electrically connected with the top electrodes 60a and 60b through wirings 61. As a material of the substrate 43, a material resisting the propagation of the ultrasound is suitable. In this embodiment, glass is used. The electrodes 45a, 45b, 46a, 46b, 47a, 47b, 48a, 48b, 60a, and 60b are made from a film of metal such as Au or Pt and formed by a method such as evaporation. The wirings 61 are formed by wire bonding using an Au wire or the like.

Figure 5:
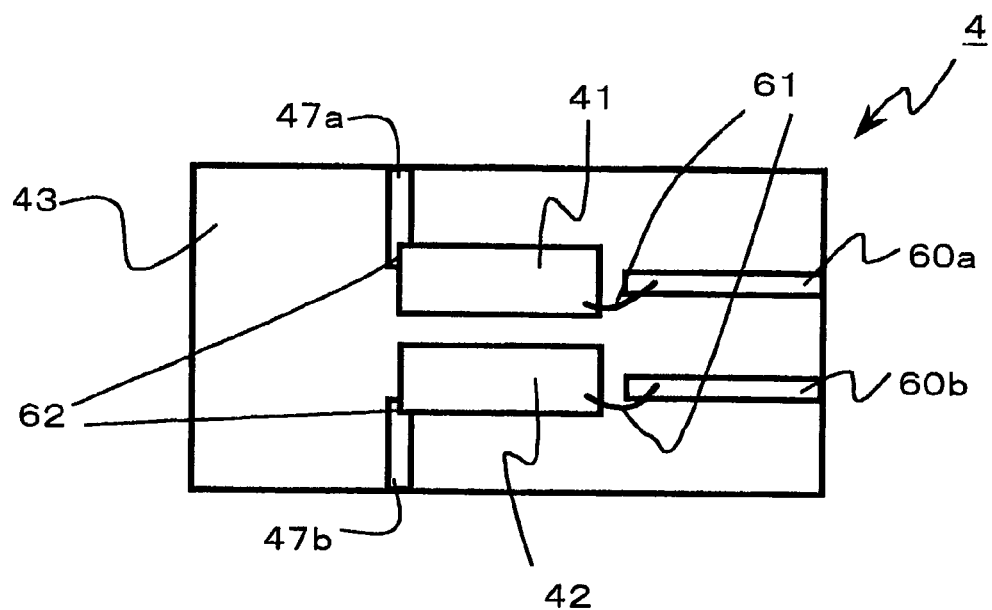
FIG. 5 is a top view of the measurement unit.

Then, as shown in FIG. 5, the transmitting piezoelectric element 41 is located and fixed on one surface 43a of the substrate 43 so as to be overlapped with the electrode 47a in a fix portion 62. Also, the receiving piezoelectric element 42 is located and fixed on one surface 43a so as to be overlapped with the electrode 47b in a fix portion 62.

Note that, as the transmitting piezoelectric element 41 and the receiving piezoelectric element 42, the same piezoelectric element may be used. Shapes of these piezoelectric elements 41 and 42 are arbitrary and piezoelectric elements with different shapes may be used for transmitting and receiving. A plurality of transmitting piezoelectric elements and a plurality of receiving piezoelectric elements may be arranged.

In this embodiment, as the transmitting piezoelectric element and the receiving piezoelectric element, a PZT having a thickness of 0.2 mm (resonance frequency is 9.6 MHz) and an outer size of 2×4 mm is used. In addition, as the substrate 43, a glass substrate having a thickness of 0.5 mm and an outer size of 10×11 mm.

In the transmitting piezoelectric element 41, the electrodes 45a and 45b are connected with the driver circuit 32 of the processing unit 3 through the electrodes 47a and 60a by wirings. When a specific drive voltage signal is applied from the driver circuit 32 to the electrodes 45a and 45b of the transmitting piezoelectric element 41, the transmitting piezoelectric element 41 is excited to generate an ultrasound with a specific frequency. Thus, the ultrasound is transmitted into the living body (see "2" in FIG. 6). In this embodiment, the transmitting piezoelectric element 41 is excited at 9.6 MHz. In the receiving piezoelectric element 42, the electrodes 46a and 46b are connected with the processing arithmetic unit 31 of the processing unit 3 through the electrodes 47b and 60b by wirings. When the ultrasound is received from the living body, the receiving piezoelectric element 42 converts the received ultrasound into a voltage signal and outputs it to the processing arithmetic unit 31 of the processing unit 3.

Figure 6:
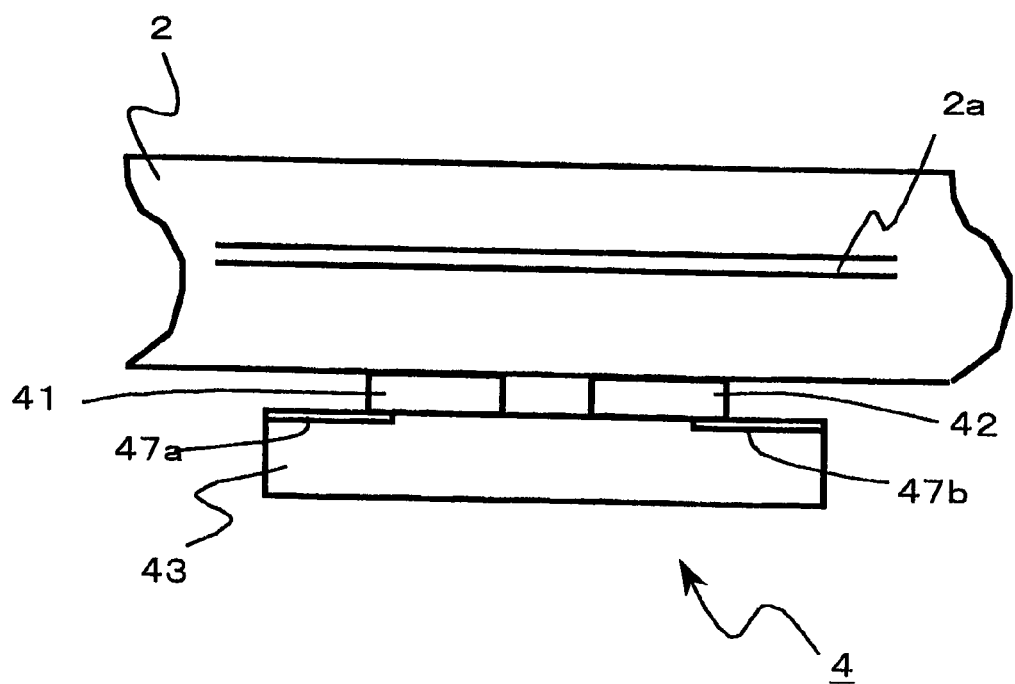
FIG. 6 shows a state in which the measurement unit is located in contact with the living body.

Next, operations of the processing unit 3 and the measurement unit 4 in the pulse detecting device 1 will be described with reference to FIGS. 3 and 6. FIG. 6 shows a location relation between the measurement unit 4 of the pulse detecting device according to this embodiment and the living body 2. The electrodes 45a, 45b, 46a, 46b, 60a, and 60b and the wirings 61 are omitted.

First, when the pulse detecting device 1 is put on the living body, as shown in FIG. 6, the measurement unit 4 is located in contact with the living body 2 (vicinity of the radial artery or the ulnar artery). Then, when the pulse is detected, the processing arithmetic unit 31 shown in FIG. 3 causes the driver circuit 32 to output the specific drive voltage signal to the electrodes 45a and 45b (see FIG. 5) of the transmitting piezoelectric element 41.

The transmitting piezoelectric element 41 is excited in response to the drive voltage signal input to the electrodes 45a and 45b to generate the ultrasound, and then transmits the ultrasound into the living body 2 (see FIG. 6). The ultrasound transmitted into the living body 2 is reflected by a blood flow 2a and received in the receiving piezoelectric element 42 of the measurement unit 4. The receiving piezoelectric element 42 converts the received ultrasound into the voltage signal and outputs it from the electrodes 46a and 46b (see FIG. 5) to the processing arithmetic unit 31.

Next, the processing arithmetic unit 31 compares the frequency of the ultrasound generated by the transmitting piezoelectric element 41 with that of the ultrasound that is received in the receiving piezoelectric element 42 and changed due to a Doppler effect of the blood flow, and thus detects the pulse of the living body. Then, the processing arithmetic unit 31 causes the display unit 33 to display a pulse detection result.

Thus, the pulse detecting device 1 measures the pulse of the living body and displays its measurement result.

Next, a method of manufacturing the measurement unit 4 of the pulse detecting device according to this embodiment will be described. With respect to the transmitting piezoelectric element 41 and the receiving piezoelectric element 42, metal such as aluminum or Au is vacuum-evaporated to form the electrodes 45a, 45b, 46a, and 46b. Outer shapes are cut by dicing or the like. With respect to the substrate 43, metal such as aluminum or Au is vacuum-evaporated to form electrodes on one surface 43a and then a thin film process such as etching is performed to form the electrodes 47a, 47b, 60a, and 60b on one surface 43a.

The electrodes 45a and 45b and the electrodes 47a and 47b are fixed in the fix portions 62 by using a conductive adhesive or the like. Thus, the transmitting piezoelectric element 41 and the receiving piezoelectric element 42 are fixed onto the substrate 43.

Further, the electrodes 47a and 60a are connected with the driver circuit 32 of the processing unit 3 of FIG. 3 through wirings (not shown). The electrodes 47b and 60b are connected with the processing arithmetic unit 31.

By the above process, in this embodiment, the transmitting piezoelectric element 41 and the receiving piezoelectric element 42 are located on the substrate 43.

Therefore, since the transmitting piezoelectric element 41 and the receiving piezoelectric element 42 can be located on the substrate 43 with high precision, the pulse detecting device 1 in which the quality of the measurement unit 4 is stable with little fluctuation can be provided. Also, since the piezoelectric elements are fixed onto the substrate 43 only in the fix portions 62 of FIG. 5, the ultrasound is unlikely to directly propagate to the substrate 43 and the noise is decreased. Thus, the detection sensitivity of the pulse can be improved. According to this embodiment, in the case where the sizes of the transmitting piezoelectric element and the receiving piezoelectric element are 2×4 mm and the size of the substrate is 10×11 mm, the areas of the fix portions 62 are set to be 0.5 mm×0.5 mm.

In the case where the transmitting piezoelectric element 41 and the receiving piezoelectric element 42 are fixed onto the entire surface of the substrate 43 by using a conductive adhesive or the like, when a burst signal (five sine waves) with ±5 V and 9.5 MHz is inputted to the transmitting piezoelectric element 41, in a state in which the measurement of the pulse is not being performed (non-measurement state), a burst signal with 0.8% of the amplitude of the inputted burst signal is received in the receiving piezoelectric element 42. However, according to this embodiment, when the fixation is made in only the fix portions 62, an amplitude of a burst signal detected in the receiving piezoelectric element is decreased to 0.02% of the amplitude of the inputted burst signal.

Further, using the measurement unit 4 of this embodiment, a reflection strength of the ultrasound for a Cu plate provided in silicon oil (rate at which the ultrasound transmitted from the transmitting piezoelectric element 41 is reflected by the Cu plate and then detected in the receiving piezoelectric element 42) was measured. As a result, when the piezoelectric elements are fixed onto the entire surface of the substrate 43, the reflection strength is 0.2%. However, when the piezoelectric elements are fixed only in the fix portions 62 on the substrate 43, as this embodiment, the reflection strength becomes 0.6% that is about three times larger than the case of the fixation in the entire surface. Therefore, the detection sensitivity of the pulse is improved.

The piezoelectric elements are not embedded in the resin for the fixation as was conventionally the case. Thus, electrodes can be easily formed on both surfaces of the transmitting piezoelectric element 41 and the receiving piezoelectric element 42, and can be easily led from the respective piezoelectric elements.

The pulse detecting device of this embodiment generally measures the pulse and displays its measurement-result, and further can measure the pulse wave.

According to this embodiment, the structure is used in the pulse detecting device 1 such that the processing unit 3 and the measurement unit 4 are separated from each other. However, these units may be structured as one module. Thus, the number of parts in the pulse detecting device 1 is reduced and the increase in the manufacturing cost can be suppressed. Further, wirings between the processing unit 3 and measurement unit 4 can be simplified.

Also, the structure may be used such that a communication unit and the like are provided in the processing unit 3 and a pulse measurement result is transmitted to a management system in a hospital. Thus, a state of a patient on which the pulse detecting device 1 is put can be always grasped.

Note that, the detail portion of this embodiment is not limited to contents of the above embodiment, and various modifications may be naturally made within the scope not departing from the gist of the present invention. For example, in this embodiment, an excitation frequency of the piezoelectric element is set to be 9.6 MHz. However, using the piezoelectric element having a resonance frequency of about 5 MHz, even when the excitation frequency is set to be about 5 MHz, there is particularly no problem.

Embodiment 2

Figure 7:
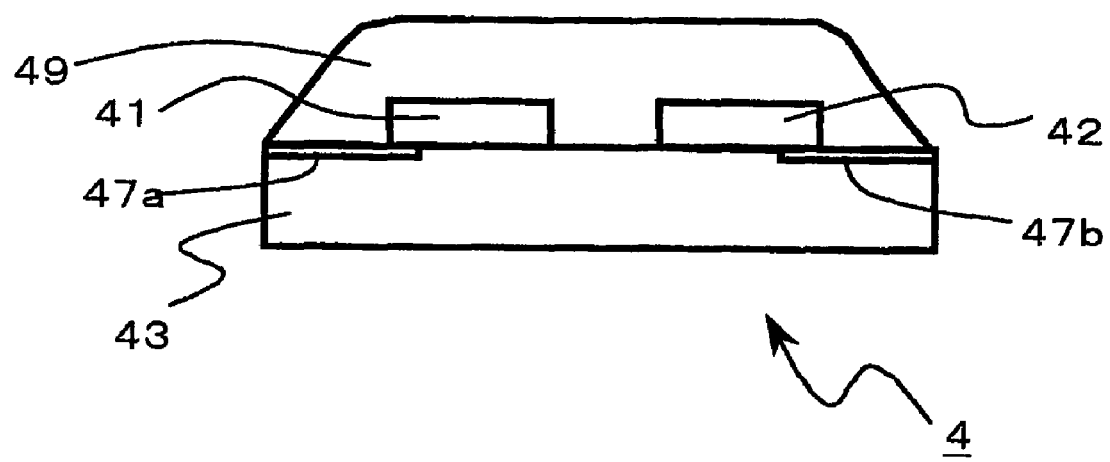
FIG. 7 is a side view of the measurement unit in which a resin layer is provided on a substrate.

A pulse detecting device according to Embodiment 2 of the present invention will be described using FIGS. 1 and 7. FIG. 7 is a side view of the measurement unit 4 in the pulse detecting device of this embodiment, and the electrodes 45a, 45b, 60a, 60b, 46a, 46b, 47a, and 47b and the wirings 61 are omitted. With respect to materials and shapes of the processing unit, the band, the clip, the piezoelectric elements, and the substrate, the same ones as in Embodiment 1 are used.

FIG. 7 shows a structure of the measurement unit 4 in which a resin layer 49 is provided on one surface 43a of the substrate 43. As shown in FIG. 7, the resin layer 49 is formed on one surface 43a of the substrate 43. Here, the resin layer 49 is made of epoxy based resin or silicon based resin. Also, the resin layer 49 has an effect for the protection of the transmitting piezoelectric element 41 and the receiving piezoelectric element 42, an effect for the insulation of the electrodes 45a, 45b, 60a, 60b, 46a, 46b, 47a, and 47b and the wirings 61, and an effect for the propagation of the ultrasound between the living body and the respective piezoelectric elements 41 and 42 with high efficiency.

In order to propagate the ultrasound between the living body and the respective piezoelectric elements 41 and 42 with high efficiency, it is required that the acoustic impedance of the resin layer 49 is set to be a value between the acoustic impedance Zl of the living body and the acoustic impedance Zc of the piezoelectric element. The acoustic impedance is a value indicating the ease with which an acoustic wave propagates. This value is changed by Young's modulus and a density.

Then, in the measurement unit 4 having the structure shown in FIG. 7, an ideal acoustic impedance Zm of the substrate 43 can be represented by the following equation, $$Zm=(Zc \times ZL)^{1/2} \quad (1).$$

Here, when ZL=1.5 M (N·sec/m$^3$) which is known and Zc (use PZT)=30 M (N·sec/m$^3$) are substituted into the equation (1), Zm=about 6.7 M (N·sec/m$^3$) is obtained.

Based on this calculation value, in this embodiment, epoxy based resin having an acoustic impedance of about 3 M (N·sec/m$^3$) is used for the substrate 43.

In addition, it is preferable that the thickness of the resin layer 49 in a substrate thickness direction is as thin as possible. In the structure as this embodiment, it is suitable to be 100 ìm or thinner. When the resin 49 is applied onto the substrate 43 by a spin coat or a bar coat and then cured by heating or ultraviolet radiation, the resin layer 49 can be uniformly located with a constant thickness.

Note that, the resin layer made of epoxy based resin may be formed on one surface 43a of the substrate 43 and then the resin layer made of silicon based resin may be formed thereon to obtain a two-layer resin layer. Thus, the reflection and the attenuation of the ultrasound can be prevented.

When the silicon based resin is used for the resin layer 49, since the silicon based resin is soft, the adhesiveness between the substrate 43 and the living body is improved by the resin layer 49. Thus, an air layer present between the living body and the substrate 43 can be decreased and the attenuation in an oscillation of the ultrasound due to the air layer can be suppressed. In addition, the silicon based resin has high compatibility with the living body. Thus, even if this resin is in closely contact with the skin, the influence to the skin is small.

Embodiment 3

Figure 8:
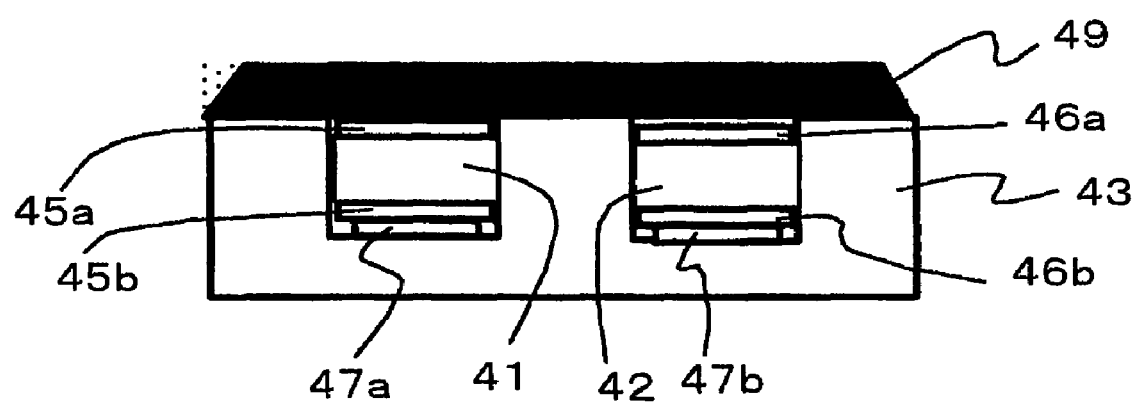
FIG. 8 shows a structure in which grooves are formed in the substrate and piezoelectric elements are embedded in the grooves.

A measurement unit 4 of a pulse detecting device 1 according to Embodiment 3 of the present invention will be described referring to FIG. 8. FIG. 8 is a side view of the measurement unit 4 in the pulse detecting device of the present invention and the wirings 61 and the electrodes 60a and 60b are omitted. With respect to materials and shapes of the processing unit, the band, the clip, the piezoelectric elements, and the substrate, the same ones as in Embodiment 1 are used. In the pulse detecting device of this embodiment, grooves are formed in the substrate 43, the electrodes 47a and 47b are formed in the grooves, the transmitting piezoelectric element 41 and the receiving piezoelectric element 42 are located in the grooves, and the resin layer 49 is attached onto the substrate 43. Therefore, when the piezoelectric elements are embedded in the grooves, as described above, the unevenness due to the piezoelectric elements is not produced and thus the resin layer 49 can be formed with further uniformity.

Embodiment 4

Figure 9:
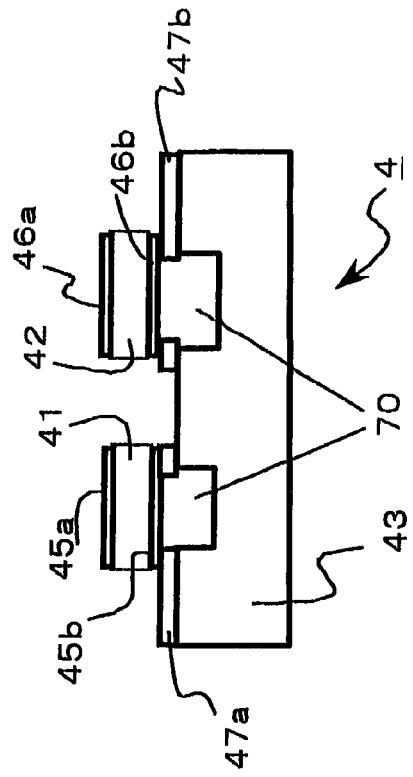
FIG. 9 shows a structure in which the substrate and the piezoelectric elements are joined to each other by bumps.

A measurement unit 4 of a pulse detecting device 1 according to Embodiment 4 of the present invention will be described referring to FIG. 9. FIG. 9 is a side view of the measurement unit 4 in the pulse detecting device of the present invention. With respect to materials and shapes of the processing unit, the band, the clip, the piezoelectric elements, and the substrate, the same ones as in Embodiment 1 are used. The electrodes 60a and 60b and the wirings 61 are omitted. In this embodiment, bumps 71 made of solder or the like are formed on the electrodes 47a and 47b. The transmitting piezoelectric element 41 and the receiving piezoelectric element 42 are fixed onto the electrodes 47a and 47b by the bumps 71. Thus, gaps 70 are produced between the transmitting piezoelectric element 41 and the electrode 47a and between the receiving piezoelectric element 42 and the electrode 47b.

In this embodiment, the bumps 71 are formed using the solder and the height of the bumps 71 is set to be 10 ìm.

An air layer has an extremely high attenuation factor for the ultrasound. Therefore, when the gaps 70 as the air layer are present, the possibility that the ultrasound is propagated into the substrate 43 and directly received in the receiving piezoelectric element 42 becomes lower. Thus, the generation of noise in the pulse measurement can be prevented.

In this embodiment, the bumps are formed for both the transmitting piezoelectric element 41 and the receiving piezoelectric element 42. Even when the bumps are formed for either the transmitting piezoelectric element 41 or the receiving piezoelectric element 42, the same effect can be obtained. In addition, the resin layer may be provided as in Embodiment 2.

Embodiment 5

Figure 10:
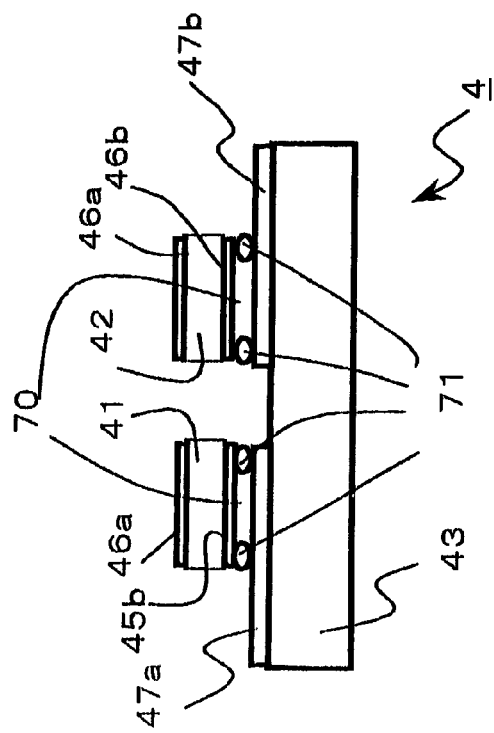
FIG. 10 shows a structure of the measurement unit having the substrate in which gaps are produced by the grooves.

A measurement unit 4 of a pulse detecting device 1 according to Embodiment 5 of the present invention will be described referring to FIG. 10. FIG. 10 is a side view of the measurement unit 4 in the pulse detecting device of this embodiment. With respect to materials of the processing unit, the band, the clip, the piezoelectric elements, and the substrate, the same ones as in Embodiment 1 are used. The electrodes 60a and 60b and the wirings 61 are omitted. The pulse detecting device of this embodiment is constructed by providing the gaps 70 between the substrate 43 and the transmitting piezoelectric element 41 and the receiving piezoelectric element 42. The gaps 70 are produced on the substrate 43. The transmitting piezoelectric element 41 and the electrode 47a and the receiving piezoelectric element 42 and the electrode 47b are located sandwiching the gaps 70.

An air layer has an extremely high attenuation factor for the ultrasound. Therefore, by the gaps 70, the possibility that the ultrasound is propagated into the substrate 43 and directly received in the receiving piezoelectric element 42 becomes lower. Thus, the generation of noise in the pulse measurement can be prevented. Further, the detection sensitivity can be improved.

Also, with respect to a distance propagation characteristic of the ultrasound, an odd multiple of a quarter of a wavelength ë, which corresponds to the peak of a wave, is preferable, in particular, about a quarter is suitable. On the other hand, it is known that, as the propagation distance is lengthened, the ultrasound is largely attenuated in a gas, a liquid, or a solid. In this embodiment, when a thickness (depth) of the gaps 70 corresponds to the wavelength ë of the ultrasound or more, the ultrasound is sufficiently attenuated and thus a preferable characteristic is obtained. For example, when an ultrasound with 9.5 MHz is used, the thickness (depth) of the gaps 70 is suitable to be 0.2 mm or more.

In the case of this embodiment, when a burst signal (five sine waves) with ±5 V and 9.5 MHz is inputted to the transmitting piezoelectric element 41, with non-measurement state, a signal with 0.02% is propagated from the transmitting piezoelectric element 41 to the receiving piezoelectric element 42. Also, a reflection strength of the ultrasound for a Cu plate provided in silicon oil (rate at which the ultrasound transmitted from the transmitting piezoelectric element 41 is reflected by the Cu plate and then detected in the receiving piezoelectric element 42) was measured. As a result, the reflection strength is 0.7%, and is further improved.

Note that, in this embodiment, the substrate 43 is diced to produce the gaps 70. However, other processing method may be used. In addition, the depth of the gaps 70 is set to be about 0.2 mm. The resin layer may be provided as in Embodiment 2.

Embodiment 6

Figure 11:
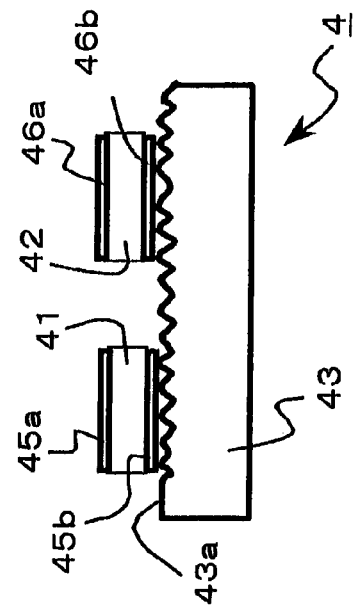
FIG. 11 shows a structure of the measurement unit having the substrate in which protrusions are formed.

A measurement unit 4 of a pulse detecting device 1 according to Embodiment 6 of the present invention will be described referring to FIG. 11. FIG. 11 is a side view of the measurement unit 4 in the pulse detecting device of this embodiment and the electrodes 47a, 47b, 60a, and 60b and the wirings 61 are omitted. With respect to materials of the processing unit, the band, the clip, the piezoelectric elements, and the substrate, the same ones as in Embodiment 1 are used.

In the pulse detecting device of this embodiment, protrusions 72 are provided for the transmitting piezoelectric element 41 and the receiving piezoelectric element 42 on the substrate 43. Since the transmitting piezoelectric element 41 and the receiving piezoelectric element 42 are fixed by only the protrusions 72, the ultrasound emitted from the transmitting piezoelectric element 41 is unlikely to directly propagate to the receiving piezoelectric element 42. Thus, the generation of noise in the pulse measurement can be prevented.

In this embodiment, the protrusions 72 are formed by plating metal such as copper on the substrate 43. However, the protrusions 72 may be formed on the substrate 43 by dicing or the like. The resin layer may be provided as in Embodiment 2.

Embodiment 7

Figure 12:
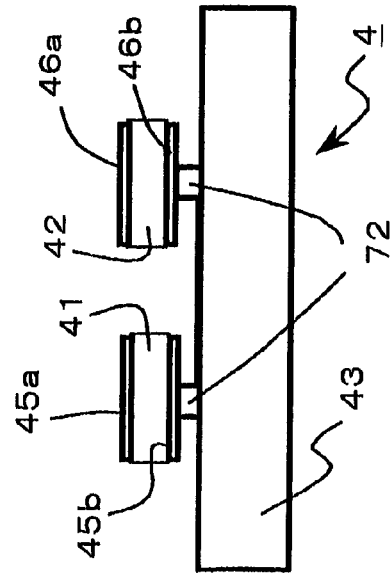
FIG. 12 shows a structure of the measurement unit having the surface-processed substrate.

A measurement unit 4 of a pulse detecting device 1 according to Embodiment 7 of the present invention will be described referring to FIG. 12. FIG. 12 is a side view of the measurement unit 4 in the pulse detecting device of this embodiment and the electrodes 60a and 60b and the wirings 61 are omitted. With respect to materials of the band, the clip, the processing unit, the piezoelectric elements, and the substrate, the same ones as in Embodiment 1 are used.

In the pulse detecting device of this embodiment, a surface processing is made for one surface 43a of the substrate 43 with a fixed roughness by grinding or the like. That is, electrodes (not shown) are provided on one surface 43a of the substrate 43. The surface processing is made with a certain roughness by grinding or the like. Then, the transmitting piezoelectric element 41 and the receiving piezoelectric element 42 are fixed onto one surface 43a by using a conductive adhesive or the like. Thus, the transmitting piezoelectric element 41 and the receiving piezoelectric element 42 are in contact with an extremely limited area of the substrate 43 through the electrodes 45b and 46b. Therefore, the ultrasound emitted from the transmitting piezoelectric element 41 is unlikely to directly propagate to the receiving piezoelectric element 42. As a result, the generation of noise in the pulse measurement can be prevented. Further, the detection sensitivity can be improved.

Embodiment 8

Figure 13:
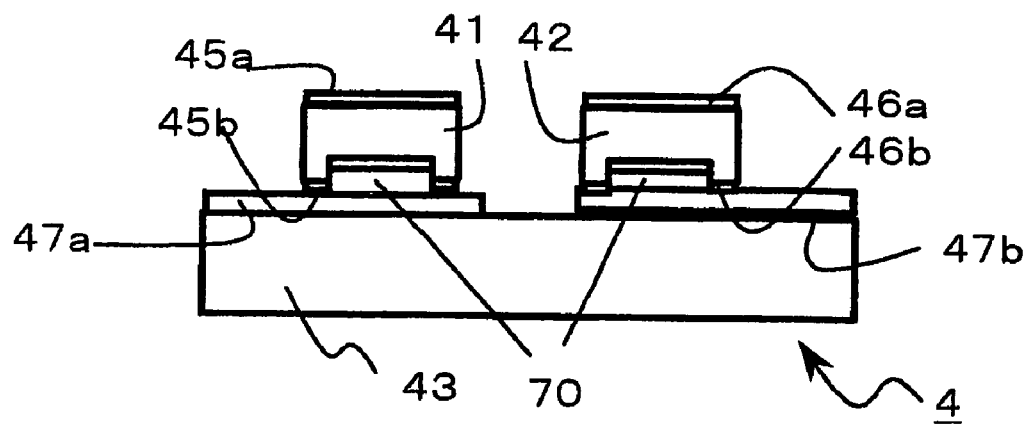
FIG. 13 shows a structure of the measurement unit having the piezoelectric elements in which the gaps are produced by the grooves.

A measurement unit 4 of a pulse detecting device 1 according to Embodiment 8 of the present invention will be described referring to FIG. 13. FIG. 13 is a side view of the measurement unit 4 in the pulse detecting device according to Embodiment 8 of the present invention and the electrodes 60a and 60b and the wirings 61 are omitted. With respect to materials and shapes of the band, the processing unit, the clip, and the substrate, the same ones as in Embodiment 1 are used.

In the pulse detecting device of this embodiment, grooves are formed in the sides of the electrodes 45b and 46b in the transmitting piezoelectric element 41 and the receiving piezoelectric element 42. The transmitting piezoelectric element 41 and the receiving piezoelectric element 42 are fixed onto the electrodes 47a and 47b through the gaps 70. The gaps 70 are produced by forming the grooves in the sides of the electrodes 45b and 46b in the transmitting piezoelectric element 41 and the receiving piezoelectric element 42 by dicing.

An air layer has an extremely high attenuation factor for the ultrasound. In addition, the transmitting piezoelectric element 41 and the receiving piezoelectric element 42 are fixed onto the substrate 43 through the gaps 70. Therefore, the ultrasound is attenuated by the gaps 70 and the ultrasound emitted from the transmitting piezoelectric element 41 is unlikely to directly propagate to the receiving piezoelectric element 42. Thus, the generation of noise in the pulse measurement can be prevented. In addition, the resin layer may be provided as in Embodiment 2.

In addition, the resin layer may be provided as in Embodiment 2. Further, a polarization processing may be made for only portions of the transmitting piezoelectric element 41 and the receiving piezoelectric element 42, which correspond to the gaps 70 in a piezoelectric element thickness direction. In this case, the above effect can be further improved.

Embodiment 9

Figure 14:
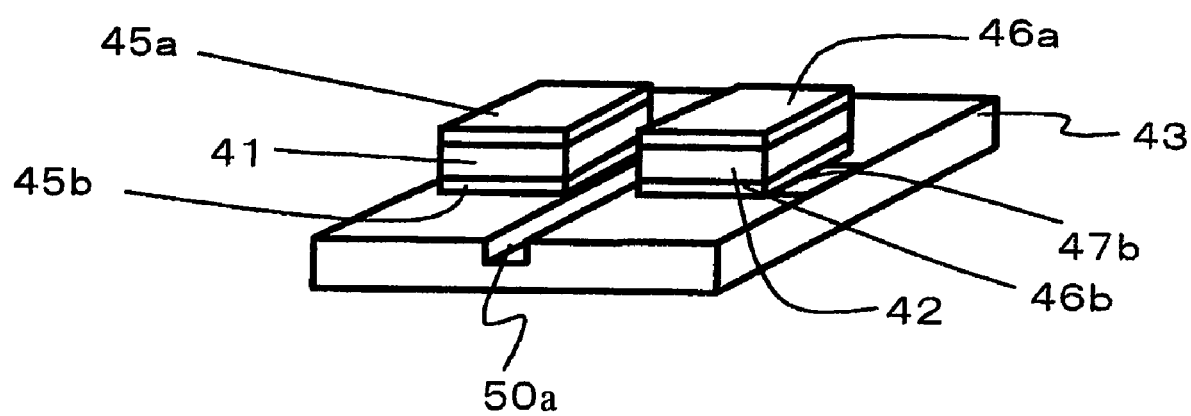
FIG. 14 shows a structure of the measurement unit having the substrate in which the grooves are formed.

A measurement unit 4 of a pulse detecting device 1 according to Embodiment 9 of the present invention will be described referring to FIG. 14. FIG. 14 is a side (perspective) view of the measurement unit 4 and the electrodes 60a and 60b and the wirings 61 are omitted. With respect to materials and shapes of the piezoelectric elements and the substrate, the same ones as in Embodiment 1 are used.

According to the structure of the pulse detecting device of this embodiment, a groove 50a is formed in the substrate 43. Then, the electrodes 45b and 46b and the electrodes 47a and 47b of the transmitting piezoelectric element 41 and the receiving piezoelectric element 42 are fixed sandwiching the groove 50a. At the pulse detection, the ultrasound emitted from the transmitting piezoelectric element 41 is reflected and attenuated by the groove 50a of the substrate 43. Therefore, the possibility that the ultrasound is propagated into a transmitting and receiving substrate 50 and directly received in the receiving piezoelectric element 42 becomes lower. Thus, the generation of noise in the pulse measurement can be prevented.

In this embodiment, the groove 50a is processed in the substrate 43 by dicing. In addition, the resin layer may be provided as in Embodiment 2.

Embodiment 10

Figure 15:
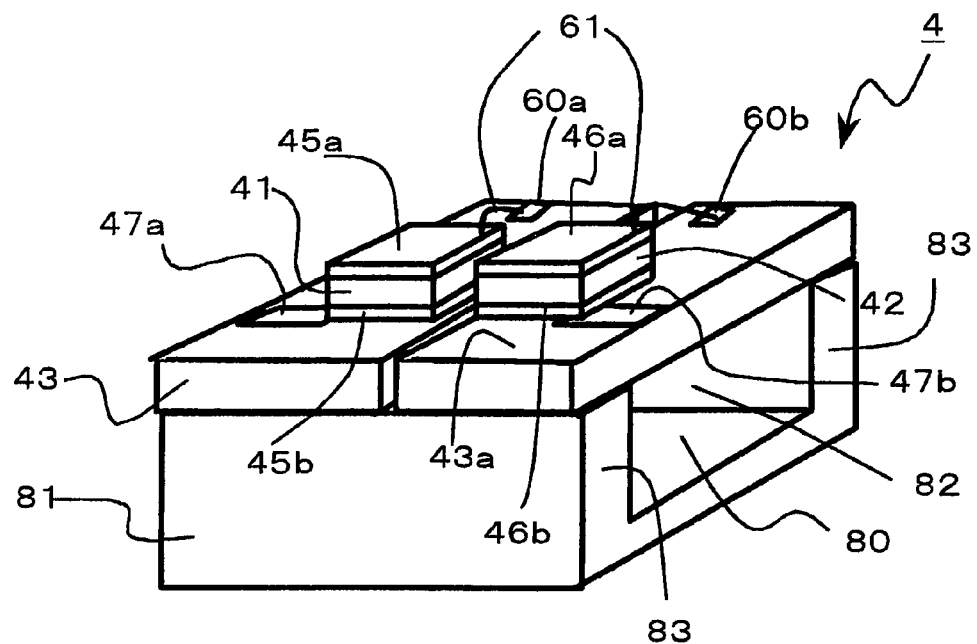
FIG. 15 shows a structure of the measurement unit having the divided substrates and a support.

A measurement unit 4 of a pulse detecting device 1 according to Embodiment 10 of the present invention will be described referring to FIG. 15. FIG. 15 is a perspective view showing a schematic structure of the measurement unit 4 in the pulse detecting device according to this embodiment. With respect to the band, the clip, the processing unit, and the piezoelectric elements, the same ones as in Embodiment 1 are used.

In the structure of the pulse detecting device of this embodiment, the substrate 43 is divided into two spaced-apart substrate sections and the transmitting piezoelectric element 41 and the receiving piezoelectric element 42 are disposed on and fixed to top surfaces of respective ones of the substrate sections. In addition, a support or support member 81 is attached onto the bottom surfaces of the substrate sections of the divided substrate 43. As shown in FIG. 15, the support 81 has a concave shape defined by two side wall portions 83,83 interconnected by a base portion. A gap 80 is produced between the substrate 43 and the support 81. Even when the substrate 43 is divided as shown in FIG. 15, the substrate 43 can be easily provided with high precision. In addition, the transmitting strength and the receiving strength of the ultrasound can be improved.

Figure 22:
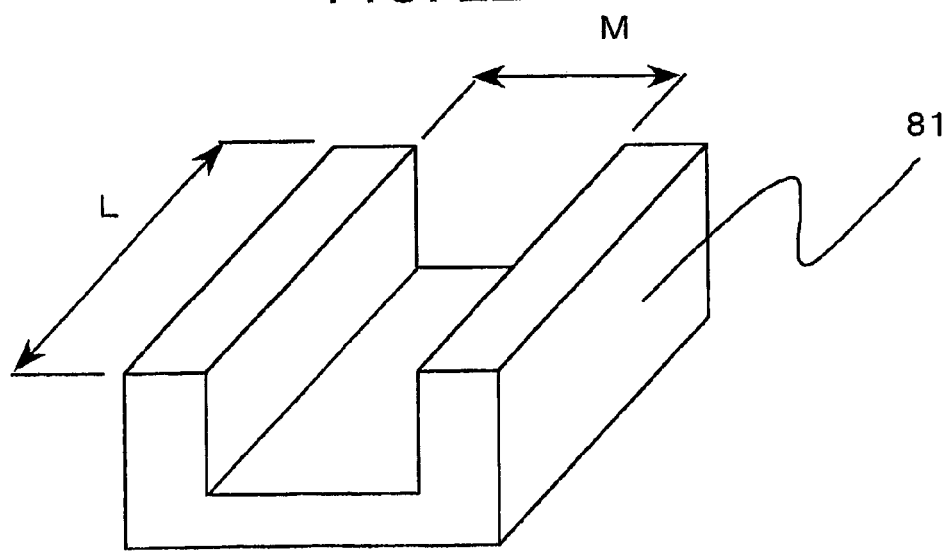
FIG. 22 shows one embodiment of the support (81)

Note that, when the cross-sectional area of the gap 80, which corresponds to an opening portion in a concave portion 82 of the support 81 (L X M in FIG. 22), is smaller than the total area of a transmit plane of the transmitting piezoelectric element 41 and a receive plane of the receiving piezoelectric element 42, the ultrasound propagates through side wall portions 83 of the support 81. Therefore, it is desirable that the area of the concave portion 82 is larger (wider) than the total area of the transmitting piezoelectric element 41 and the receiving piezoelectric element 42.

When a burst signal (five sine waves) with ±5 V and 9.5 MHz is inputted to the transmitting piezoelectric element 41, in the case of this embodiment, an amplitude of a burst signal detected in the receiving piezoelectric element is decreased to 0.01% of that of the inputted burst signal. Further, using the measurement unit 4 of this embodiment, a reflection strength of the ultrasound for a Cu plate provided in silicon oil (rate at which the ultrasound transmitted from the transmitting piezoelectric element 41 is reflected by the Cu plate and then detected in the receiving piezoelectric element 42) was measured. As a result, the reflection strength is improved to 1.0%.

Even if the ultrasound generated by the transmitting piezoelectric element 41 is propagated to the substrate 43, since the gap 80 is present between the substrate 43 and the support 81, the ultrasound is attenuated and thus is not propagated to the support 81. Therefore, the ultrasound emitted from the transmitting piezoelectric element 41 is unlikely to directly propagate to the receiving piezoelectric element 42. As a result, the generation of noise in the pulse measurement can be prevented. Further, the detection sensitivity can be improved.

In this embodiment, acrylic is used as the support 81. However, when the support 81 is formed using a porous material in which the ultrasound is easily attenuated, or the like, the ultrasound emitted from the transmitting piezoelectric element 41 is unlikely to directly propagate to the receiving piezoelectric element 42. Thus, the generation of noise in the pulse measurement can be prevented. In addition, the resin layer may be provided as in Embodiment 2.

Embodiment 11

Figure 16:
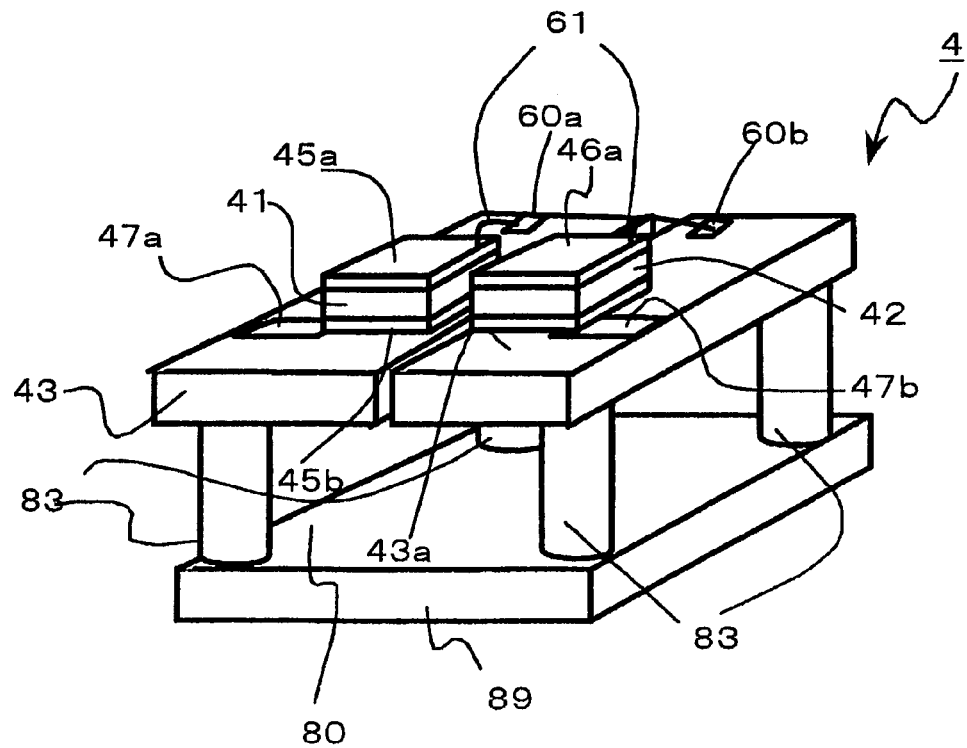
FIG. 16 shows a structure of the measurement unit having the divided substrates and the support.

A measurement unit 4 of a pulse detecting device 1 according to Embodiment 11 of the present invention will be described referring to FIG. 16. FIG. 16 is a perspective view showing a schematic structure of the measurement unit 4 in the pulse detecting device according to this embodiment. With respect to materials of the band, the processing unit, the clip, the piezoelectric elements, and the substrate, the same ones as in Embodiment 1 are used.

In the structure of the measurement unit of the pulse detecting device according to this embodiment, the substrate 43 is divided into two spaced-apart substrate sections and the transmitting piezoelectric element 41 and the receiving piezoelectric element 42 are disposed on and fixed to top surfaces of the respective substrate sections. In addition, a support or support member 89 is attached onto the bottom surface of the substrate 43 through columnar projections in the form of posts 83. Even when the substrate 43 is divided as shown in FIG. 16, the substrate 43 can be easily provided with high precision. In addition, the transmitting strength and the receiving strength of the ultrasound can be improved.

As shown in FIG. 16, the support 89 is attached onto the substrate 43 through the posts 83. Even if the ultrasound generated by the transmitting piezoelectric element 41 is propagated to the substrate 43, since the gap 80 is present between the substrate 43 and the support 89, the ultrasound is attenuated and thus is not propagated to the support 89. Therefore, the ultrasound emitted from the transmitting piezoelectric element 41 is unlikely to directly propagate to the receiving piezoelectric element 42. As a result, the generation of noise in the pulse measurement can be prevented. Further, the detection sensitivity can be improved.

In this embodiment, acrylic is used as the support 89. However, when the support 89 is formed using a porous material in which the ultrasound is easily attenuated, or the like, the ultrasound emitted from the transmitting piezoelectric element 41 is unlikely to directly propagate to the receiving piezoelectric element 42. Thus, the generation of noise in the pulse measurement can be prevented. In addition, a resin layer may be provided as in Embodiment 2.

Embodiment 12

Figure 17:
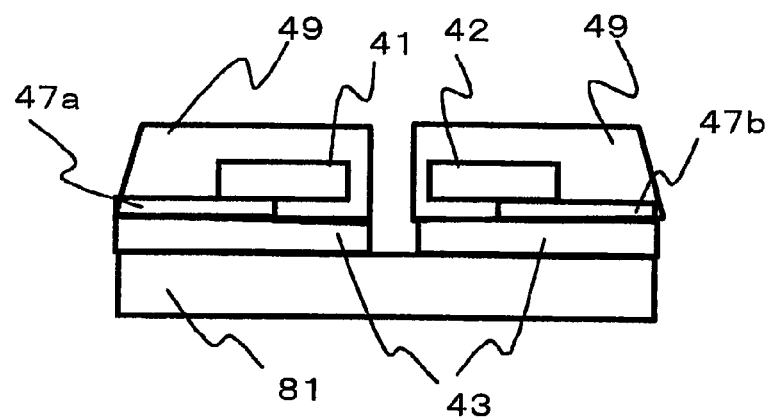
FIG. 17 shows a structure of the measurement unit having the divided substrates and the support.

A measurement unit 4 of a pulse detecting device 1 according to Embodiment 12 of the present invention will be described referring to FIG. 17. FIG. 17 is a side view of the measurement unit 4 in the pulse detecting device according to this embodiment. With respect to materials of the band, the processing unit, the clip, the piezoelectric elements, and the substrate, the same ones as in Embodiment 1 are used. The electrodes 45a, 45b, 46a, 46b, 60a and 60b and the wirings 61 are omitted.

In the structure of the measurement unit of the pulse detecting device according to this embodiment, the substrate 43 is divided into the side of the transmitting piezoelectric element 41 and the side of the receiving piezoelectric element 42. In addition, the support 89 is attached onto the other surface of the substrate 43. Further, the resin layer 49 is divided into the side of the transmitting piezoelectric element 41 and the side of the receiving piezoelectric element 42. When the resin layer is divided and provided on the substrate 43, there is a following effect. That is, the ultrasound received in the receiving piezoelectric element 42 through the resin layer 49 without propagating it into the living body from the transmitting piezoelectric element 41 is decreased, and thus the detection sensitivity of the pulse is improved. When a material such as a porous material (such as ceramic) or rubber, in which the ultrasound is easily attenuated, is used as the support 81, it can prevent the ultrasound from propagating from the transmitting piezoelectric element 41 to the receiving piezoelectric element 42 through the support 81.

Embodiment 13

Hereinafter, an embodiment of a pulse detecting device of the present invention will be described in detail with reference to the drawings.

A side view showing a structure in an outer appearance of the pulse detecting device 1 according to the present invention is shown in FIG. 1. In addition, a state in which the pulse detecting device 1 shown in FIG. 1 is put on the living body (wrist) 2 is shown in FIG. 2.

As shown in FIG. 1, the pulse detecting device 1 is substantially constructed by the processing unit 3, the measurement unit 4, the band 5, and the clip 6. As shown in FIG. 2, the pulse detecting device 1 is always portable by being put on the living body 2. The processing unit 3 and the measurement unit 4 are attached to the band 5, and thus these are put on the living body 2 (the broken line portion in FIG. 1) by the band 5 and the clip 6. At this time, the measurement unit 4 is located in contact with the vicinity of the radial artery or the ulnar artery in the living body 2 (not shown). In addition, although not shown, the processing unit 3 and the measurement unit 4 are connected with each other through wirings. A drive voltage signal is inputted from the processing unit 3 to the measurement unit 4 through the wirings. A voltage signal measured by the measurement unit 4 is inputted to the processing unit 3.

A block diagram showing an inner structure of the processing unit 3 of the pulse detecting device and a connection state between the processing unit 3 and the measurement unit 4 are shown in FIG. 3. As shown in the drawing, the processing unit 3 is substantially constructed by the processing arithmetic unit 31, the driver circuit 32, and the display unit 33.

The processing arithmetic unit 31 executes a processing program stored in a memory region (not shown) provided in the inner portion to perform various processings with respect to the detection of the pulse and causes the display unit 33 to display the processing result. Also, the processing arithmetic unit 31 causes the driver circuit 32 to output a specific drive voltage signal to the transmitting piezoelectric element 41 (described later with respect to details) of the measurement unit 4 when the pulse is measured. Further, the processing arithmetic unit 31 compares the frequency of the ultrasound emitted from the transmitting piezoelectric element 41 with that of the ultrasound that is received in the receiving piezoelectric element 42 and changed due to a Doppler effect of blood flow, and thus detects the pulse.

The driver circuit 32 outputs a specific drive voltage signal to the transmitting piezoelectric element 41 of the measurement unit 4 in response to instructions of the processing arithmetic unit 31.

The display unit 33 is composed of a liquid crystal display screen and the like, and displays a pulse detection result and the like that are inputted from the processing arithmetic unit 31.

Figure 18:
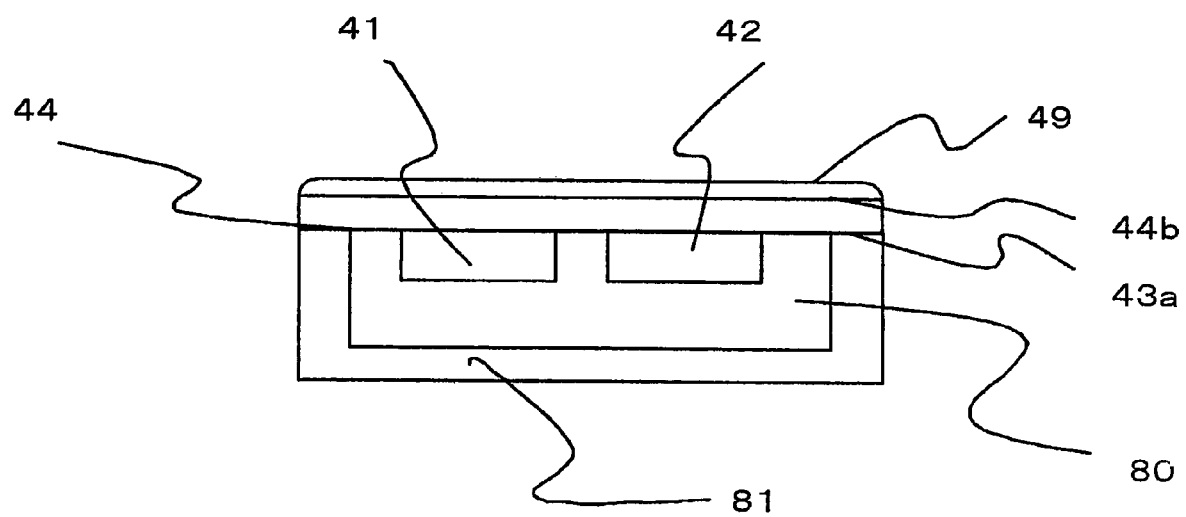
FIG. 18 shows one embodiment of the measurement unit (4)

Next, a cross sectional view of the measurement unit 4 of the pulse detecting device 1 is shown in FIG. 18. The transmitting piezoelectric element 41 and the receiving piezoelectric element 42 are joined onto a receiving and transmitting substrate 44. The receiving and transmitting substrate 44 is supported by the support 81. By such a structure, a space 80 can be produced over one surface of the respective piezoelectric elements. Thus, the transmitting piezoelectric element 41 and the receiving piezoelectric element 42 can propagate the ultrasound only in ultrasound transmitting and receiving directions.

When the transmitting piezoelectric element 41 and the receiving piezoelectric element 42 are joined onto the receiving and transmitting substrate 44, there is a method using various adhesives or a method using diffusion bond or eutectic bond. In the method using the diffusion bond, an application of pressure and heat are made in a state in which two metals are in contact with each other. Thus, the thermal diffusion of metal atoms is produced between the metals to make the above joining. In the method using the eutectic bond, the application of pressure and heat are made in a state in which two metals are in contact with each other to fuse the respective metals. Then, an alloy is produced between the metals by cooling to make the above joining. When the diffusion bond or the eutectic bond is used in the case where the transmitting piezoelectric element 41 or the receiving piezoelectric element 42 is joined onto the receiving and transmitting substrate 44, there is an advantage that an adhesion layer is not formed in a junction interface, and an attenuation amount of oscillation of the ultrasound in the junction interface can be decreased. Also, shapes of these piezoelectric elements 41 and 42 are arbitrary and piezoelectric elements with different shapes may be used for transmitting and receiving.

In addition, the transmitting piezoelectric element 41 is electrically connected with the driver circuit 32 of the processing unit 3 through the wirings. Thus, when the specific drive voltage signal is applied from the driver circuit 32 to the transmitting piezoelectric element 41, the transmitting piezoelectric element 41 is excited to generate the ultrasound with a specific frequency. The generated ultrasound is transmitted into the living body ("2" in FIG. 31).

The receiving piezoelectric element 42 is electrically connected with the processing arithmetic unit 31 of the processing unit 3 through the wirings. When the ultrasound is received from the living body, the receiving piezoelectric element 42 converts the received ultrasound into a voltage signal and outputs it to the processing arithmetic unit 31 of the processing unit 3.

The transmitting piezoelectric element 41 and the receiving piezoelectric element 42 are located on one surface 43a of the transmitting and receiving substrate 44. The other surface 43b thereof is in contact with the living body and made from a glass substrate or the like.

Here, in order to propagate the ultrasound with high efficiency between the living body and respective piezoelectric elements 41 and 42 through the transmitting and receiving substrate 44, it is required that the acoustic impedance of the transmitting and receiving substrate 44 is set to be a value between the acoustic impedance ZL of the living body and the acoustic impedance Zc of the piezoelectric element. The acoustic impedance is a value indicating the ease of propagating an acoustic wave. This value is changed by Young's modulus and a density.

Then, in the measurement unit 4 having the structure shown in FIG. 18, an ideal acoustic impedance Zm of the transmitting and receiving substrate 44 can be represented by the following equation, $$Zm = (Zc \times ZL)^{1/2} \qquad (1).$$

Here, when ZL=1.5 M (N·sec/m$^3$) which is known and Zc=30 M (N·sec/m$^3$) in the case of using PZT, are substituted into the equation (1), Zm=about 6.7 M (N·sec/m$^3$) is obtained.

Based on this calculation value, in this embodiment, a glass substrate having an acoustic impedance of about 10 M (N·sec/m$^3$) is used as the transmitting and receiving substrate 44.

In addition, in the propagation of the ultrasound, the thickness of the transmitting and receiving substrate 44 is an important factor. When the thickness of the transmitting and receiving substrate 44 is not suitable, as the above acoustic impedance, the ultrasound is reflected in the transmitting and receiving substrate 44 and thus is not propagated with high efficiency. Thus, it is preferable that the thickness of the transmitting and receiving substrate 44 is set to be about a quarter of the wavelength in the frequency of the ultrasound which the transmitting and receiving substrate 44 propagates. Concretely, when the frequency of the ultrasound is 9 MHz (generally, the ultrasound with 2.3 to 10 MHz is used) and the sound velocity in the transmitting and receiving substrate (glass substrate) is about 5000 m/sec., the thickness of the transmitting and receiving substrate 44 is set to be about 140 im.

Also, a resin layer 48 is formed on a surface of the transmitting and receiving substrate 44, which is opposite to a piezoelectric element forming surface, that is, a surface that is in contact with the living body. Here, the resin layer 48 is made of epoxy based resin or silicon based resin. A property of a contact surface (the other surface 43b) of the transmitting and receiving substrate 44 to the living body is different depending on a kind of resin to be used.

For example, when the epoxy based resin is used for the resin layer 48, the acoustic impedance of the epoxy based resin is the value between the acoustic impedance of the transmitting and receiving substrate 44 and that of the living body. Thus, the reflection of the ultrasound, which is produced in the interface between the living body and the transmitting and receiving substrate 44 can be further reduced. Therefore, the ultrasound can be propagated with high efficiency between the living body and the substrate 44. Here, an ideal acoustic impedance of the resin layer 48 is calculated by the same equation as the above equation (1).

Also, when the silicon based resin is used for the resin layer 48, since the silicon based resin is soft, the adhesiveness between the transmitting and receiving substrate 44 and the living body is improved by the resin layer 48. Thus, an air layer present between the living body and the transmitting and receiving substrate 44 can be decreased and the attenuation in the oscillation of the ultrasound due to the air layer can be suppressed. In addition, the silicon based resin has high compatibility with the living body. Thus, even if this resin is in close contact with the skin, the influence to the skin is small.

Note that, the resin layer made of the epoxy based resin is formed on the other surface of the transmitting and receiving substrate 44 and then the resin layer made of the silicon based resin may be formed thereon to obtain two-layer resin layers. Thus, the reflection and the attenuation of the ultrasound can be prevented.

Next, operations of the processing unit 3 and the measurement unit 4 in the pulse detecting device 1 will be described with reference to FIGS. 3 and 31.

Figure 31:
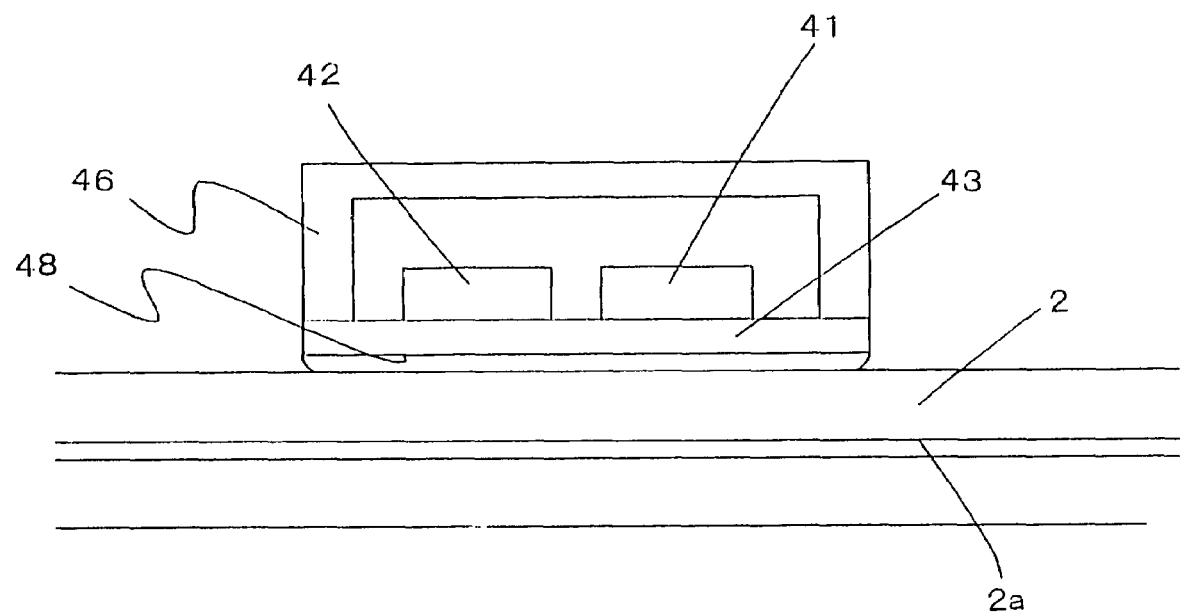
FIG. 31 shows the state in which the measurement unit is located in contact with the living body.
Figure 32:
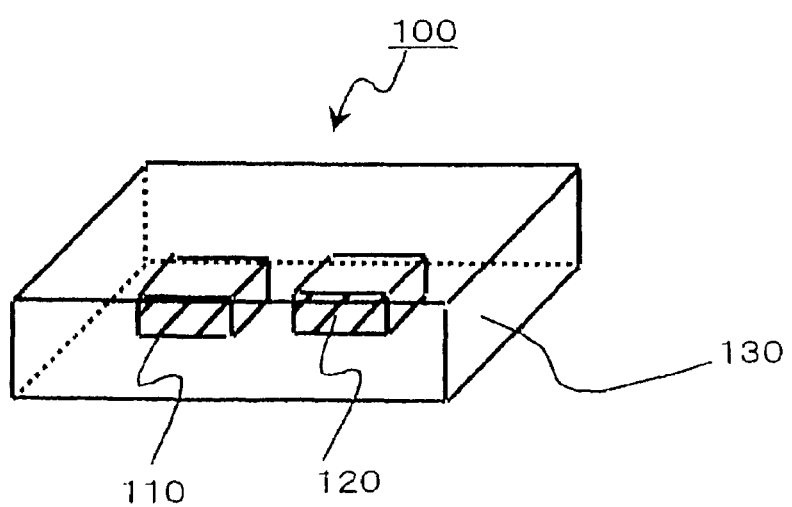
FIG. 32 shows an ultrasound diagnostic apparatus using conventional piezoelectric elements.

First, when the pulse detecting device 1 is put on the living body, as shown in FIG. 31, the measurement unit 4 is located in contact with the living body 2 (in the vicinity of the radial artery or the ulnar artery). Then, when the pulse is detected, the processing arithmetic unit 31 shown in FIG. 3 causes the driver circuit 32 to output the specific drive voltage signal to the transmitting piezoelectric element 41.

The transmitting piezoelectric element 41 is excited in response to the inputted drive voltage signal to generate an ultrasound, and then transmits the ultrasound into the living body 2 through the transmitting and receiving substrate 44. The ultrasound transmitted into the living body 2 is reflected by the blood flow 2a and received in the receiving piezoelectric element 42 of the measurement unit 4. The receiving piezoelectric element 42 converts the received ultrasound into the voltage signal and outputs it to the processing arithmetic unit 31.

Next, the processing arithmetic unit 31 compares the frequency of the ultrasound generated by the transmitting piezoelectric element 41 with that of the ultrasound that is received in the receiving piezoelectric element 42 and changed due to a Doppler effect of the blood flow, and thus detects the pulse of the living body. Then, the processing arithmetic unit 31 causes the display unit 33 to display the pulse detection result. Thus, the pulse detecting device 1 measures the pulse of the living body and displays its measurement result.

Therefore, since the transmitting piezoelectric element 41 and the receiving piezoelectric element 42 can be located on the transmitting and receiving substrate 44 with high precision, the quality of the measurement unit 4 is stable, and the pulse detecting device 1 in which the quality does not vary can be provided. In addition, the detection sensitivity of the pulse can be improved.

Also, since the pulse detecting device 1 has the support portion, the strength of the pulse detecting device 1 is increased. Thus, the durability of the pulse detecting device 1 is improved.

Further, the pulse detecting device 1 of this embodiment generally measures the pulse and displays its measurement result, and it further can measure the pulse wave.

Note that, the detail portion of the pulse detecting device of the present invention is not limited to the contents of the above embodiment, and various modifications may be naturally made in the scope not departing from the gist of the present invention. For example, in this embodiment, the transmitting piezoelectric element 41 and the receiving piezoelectric element 42 are joined onto the transmitting and receiving substrate 44 by metallic bond. However, this joining may be made by hydrogen bond. Here, in a method using the hydrogen bond, water is ionized using an ion source to produce hydroxide ions OH$^-$. After the hydroxide ions OH$^-$ are irradiated into the transmitting and receiving substrate 44, the transmitting and receiving substrate 44 and the respective piezoelectric elements 41 and 42 are pressed to each other to make the above joining. In addition, a hydrophilic group is formed on the transmitting and receiving substrate 44, and then the respective piezoelectric elements 41 and 42 may be joined onto the transmitting and receiving substrate 44 by the hydrogen bond using the hydrophilic group.

Also, as this embodiment, without using the structure such that the processing unit 3 and the measurement unit 4 in the pulse detecting device 1 are separated from each other, these units may be structured as one module. Thus, the number of parts in the pulse detecting device 1 is reduced and the increase in the manufacturing cost can be suppressed. Further, wirings between the processing unit 3 and measurement unit 4 can be simplified.

Further, the structure may be used such that a communication unit and the like are provided in the processing unit 3 and a pulse measurement result is transmitted to a management system in a hospital. Thus, a state of a patient on which the pulse detecting device 1 is put can be always grasped.

Embodiment 14

A modification example of the structure of the measurement unit 4 shown in FIG. 18 will be described with reference to FIGS. 19 to 21. Note that, in the description below, portions with the same structure as in the measurement unit 4 shown in FIG. 18 are referred with the same reference. Therefore, the duplicate explanation is omitted here.

Figure 19:
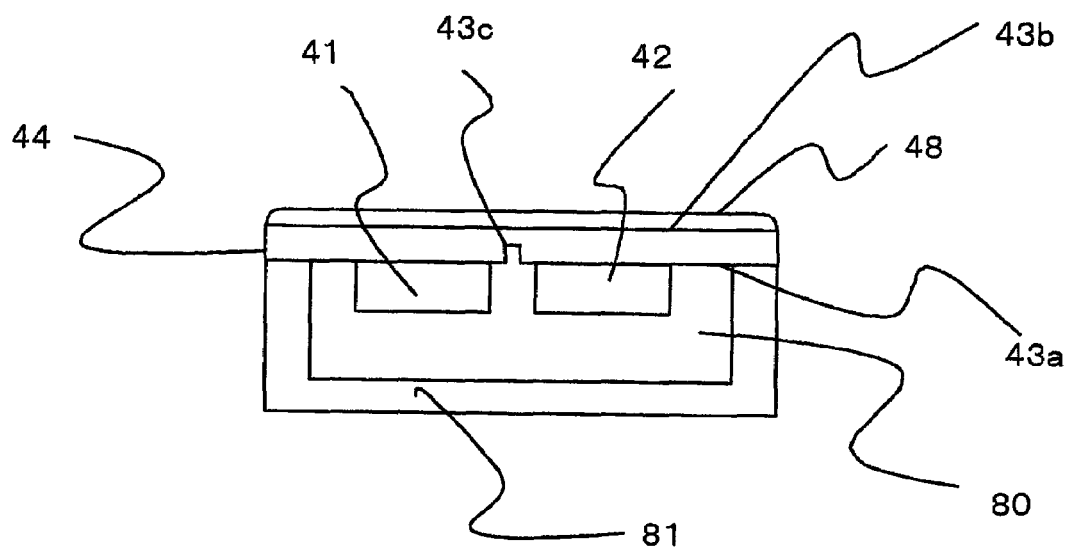
FIG. 19 shows one embodiment of the measurement unit (4)

FIG. 19 shows a structure of the measurement unit 4 in which the transmitting piezoelectric element 41 and the receiving piezoelectric element 42 are located sandwiching a groove 43c formed in the transmitting and receiving substrate 44.

As shown in FIG. 19, the groove 43c is formed in the transmitting and receiving substrate 44. The transmitting piezoelectric element 41 and the receiving piezoelectric element 42 are located sandwiching the groove 43c.

Therefore, the ultrasound emitted from the transmitting piezoelectric element 41 at the time of pulse detection is reflected and attenuated by the groove 43c of the transmitting and receiving substrate 44. As a result, the possibility that the ultrasound is propagated into the transmitting and receiving substrate 44 and directly received in the receiving piezoelectric element 42 becomes lower. Thus, the generation of noise in the pulse measurement can be prevented. Further, the detection sensitivity can be improved.

Note that, a shape of the groove 43c is arbitrary. For example, a cross sectional shape of the groove 43c may be an inverted triangle.

Embodiment 15

Figure 20:
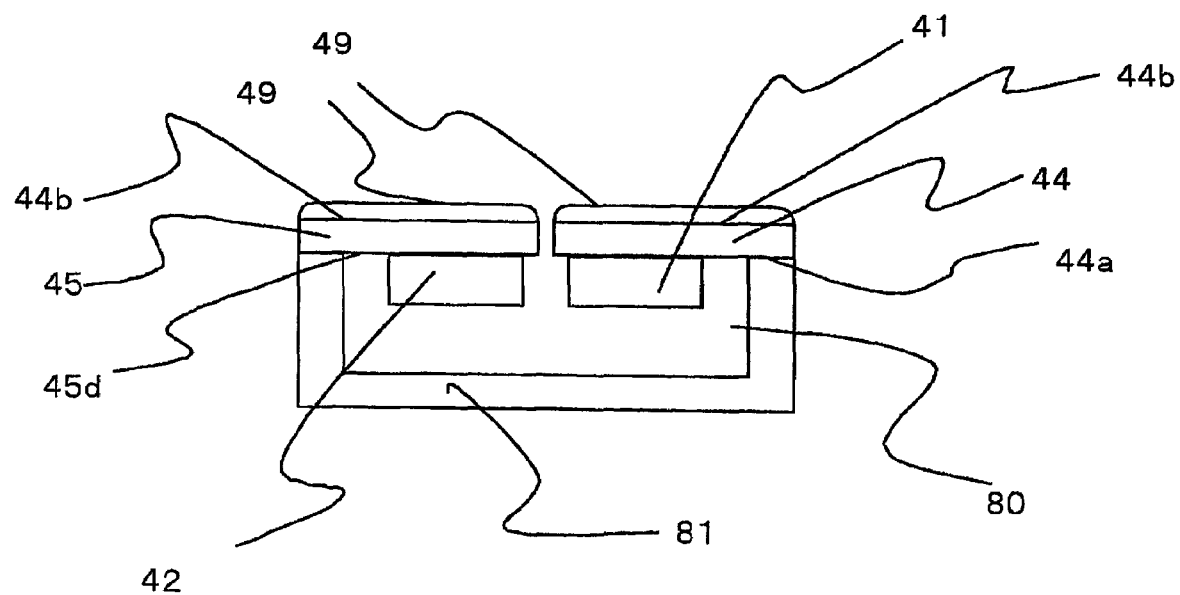
FIG. 20 shows one embodiment of the measurement unit (4)

FIG. 20 shows a structure of a measurement unit 4 in which the transmitting piezoelectric element 41 and the receiving piezoelectric element 42 are located on divided transmitting and receiving substrates or substrate sections 44 and 45. As shown in FIG. 20, in the measurement unit 4, the transmitting and receiving substrate 44 (FIG. 18) is divided into two spaced-apart non-contacting transmitting and receiving substrates (substrate sections) 44 and 45. Then the transmitting piezoelectric element 41 is located on the transmitting substrate 44 and the receiving piezoelectric element 42 is located on the receiving substrate 45.

Therefore, the ultrasound emitted from the transmitting piezoelectric element 41 at the time of pulse detection is not directly propagated to the receiving piezoelectric element 42. Thus, the generation of noise in the pulse measurement can be prevented.

Embodiment 16

Figure 21:
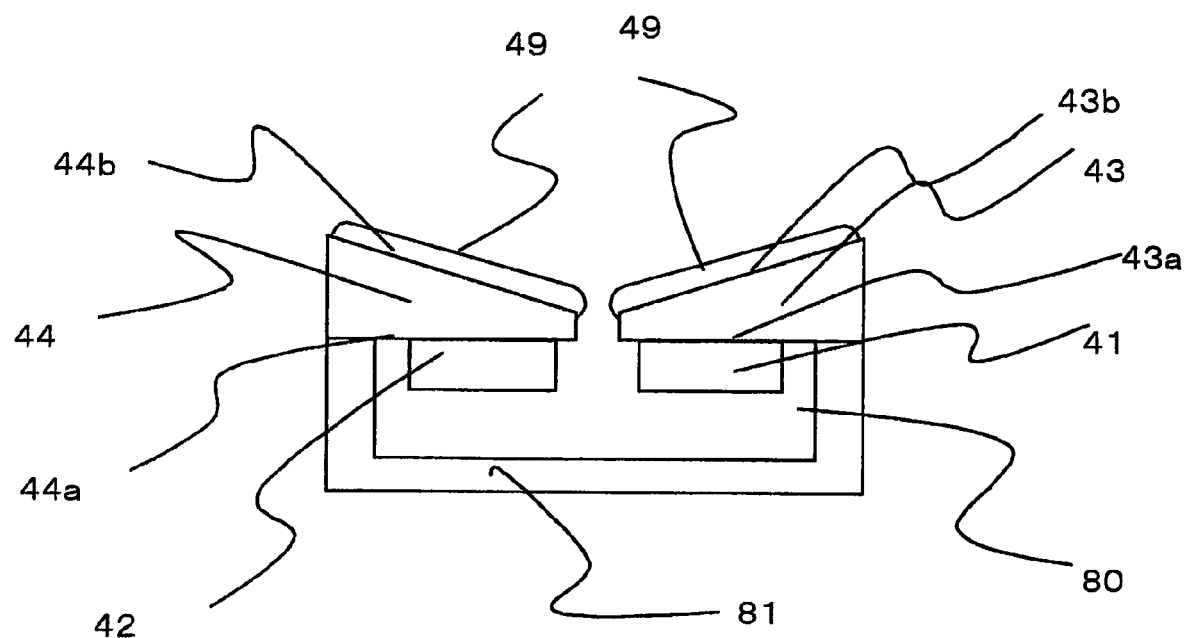
FIG. 21 shows one embodiment of the measurement unit (4)

FIG. 21 shows a structure of a measurement unit 4 in which a transmitting substrate 44 and a receiving substrate 45, which are obtained by dividing, have taper shapes. As shown in FIG. 21, in the meaurement unit 4, the transmitting and receviing substrate 44 (FIG. 18) is divided into two transmitting and receiving substrates (substrate sections) 44 and 45. Then, the transmitting piezoelectric element 41 is located on one surface (bottom surface) 44a of the transmitting substrate 44 and the receiving piezoelectric element 42 is located on one surface (bottom surface) 45a of the receiving substrate 45. The other (top) surface 44b of the transmitting and receiving substrate 44 and the other (top) surface 45b of the transmitting and receiving substrate 45 have taper shapes and are inclined relative to one another less than 180 degrees. Here, the taper shapes are formed along the direction of the blood flow of the living body and such that outside portions of the respective transmitting and receiving substrates 44 and 45 are thicker than their inside portions. Therefore, the ultrasound emitted from the transmitting piezoelectric element 41 can be easily to focused near the blood flow of the living body. Thus, the ultrasound reflected by the blood flow of the living body can be received in the receiving piezoelectric element 42 with high efficiency.

Figure 23:
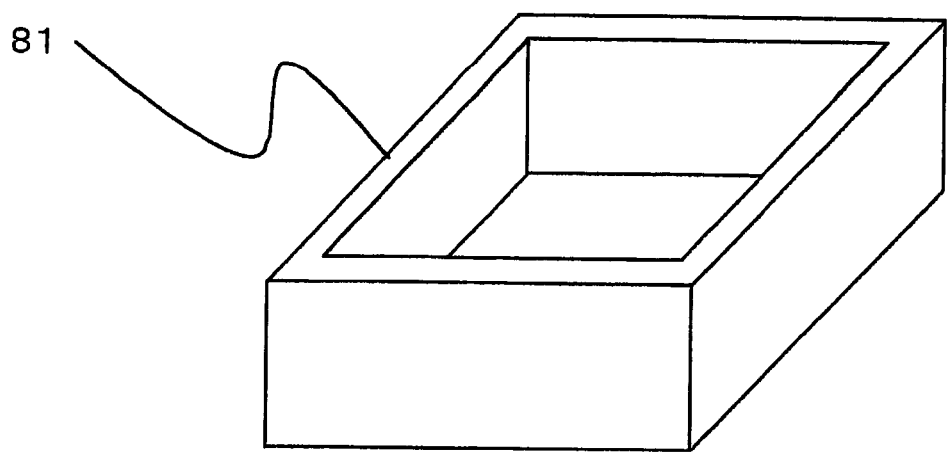
FIG. 23 shows one embodiment of the support (81)

In addition, the structure of the support is not limited to the support 81 (FIG. 22) with the concave shape as shown in FIGS. 18 to 21. A support with a box shape as shown in FIG. 23 may also be used. When the support with the box shape shown in FIG. 23 is used, the pulse detecting device with high durability can be obtained.

Figure 24:
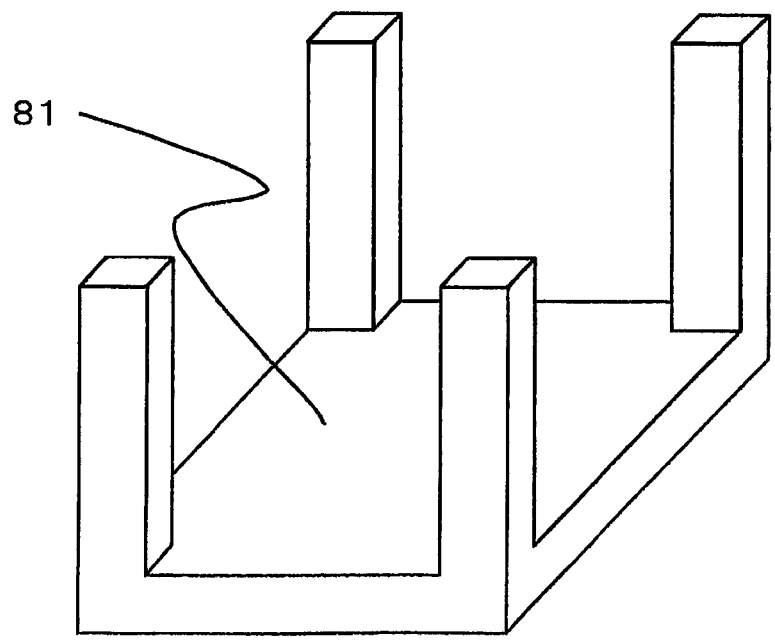
FIG. 24 shows one embodiment of the support (81)
Figure 25:
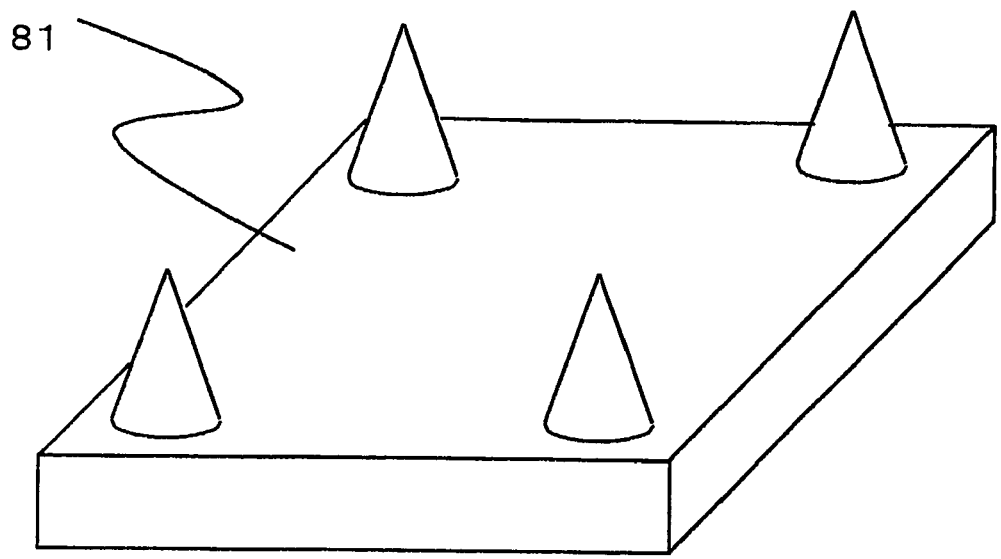
FIG. 25 shows one embodiment of the support (81)

In addition, as shown in FIG. 24, the support (support member) 81 may be formed with columnar projections in a comb teeth shape. By forming such a support, the area for holding the substrate is reduced, the amount of leakage of the ultrasound from the transmitting side to the receiving side is decreased, and the amount of noise is further decreased. Thus, the pulse detecting device with higher performance can be obtained. Also, as shown in FIG. 25, the projections may be conical prolections having tips that form acute angles, whereby the pulse detection device in which the amount of noise is further decreased can be obtained.

Figure 26:
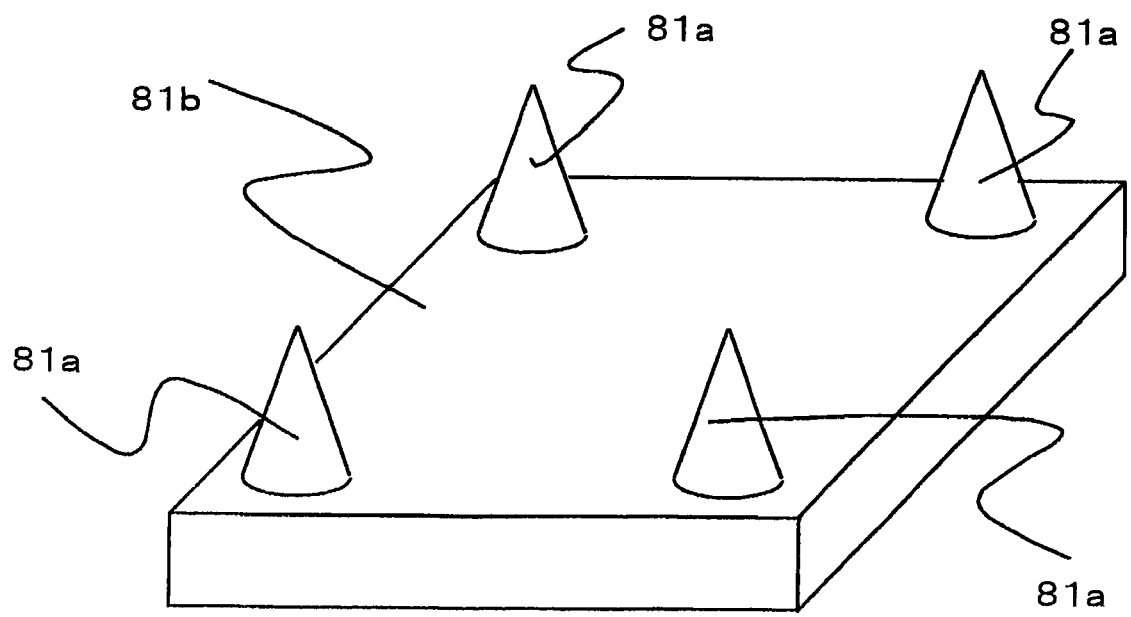
FIG. 26 shows one embodiment of the support (81)

As a material of the support 81, a metal material, an organic material, an inorganic material, or composite material of these is used. When ceramics is used for the support, since the ceramics is hard, the strength of the pulse detecting device is increased. When plastic is used for the support, it is suitable for mass production, and thus the cost is reduced. In particular, when the plastic is used, the cost is reduced without a concern for a shape by an injection molding or the like. When metal is used for the support 81, the support can be precisely processed. Therefore, when plastic and metal are used for a support as shown in FIG. 26, the pulse detecting device with low cost and low noise can be obtained. When a porous material such as ceramics or sponge is used, since the ultrasound is not propagated, the noise is reduced and thus the performance is improved.

Embodiment 17

Figure 27:
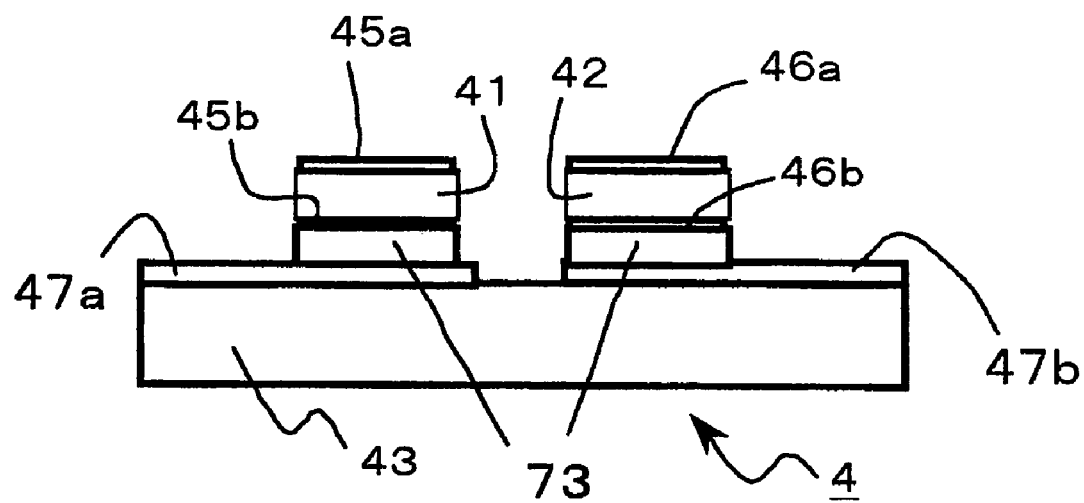
FIG. 27 shows one embodiment of the measurement unit (4)

One example of a pulse detecting device 1 as one embodiment of an ultrasound diagnostic apparatus of the present invention will be described using FIG. 27. FIG. 27 is a side view of a measurement unit 4 in the pulse detecting device of this embodiment, and the electrodes 60a and 60b and the wirings 61 are omitted. With respect to materials of the band, the clip, the processing unit, the piezoelectric elements, and the substrate, the same ones as in Embodiment 1 are used.

FIG. 27 shows the case where respective conductive rubbers as ultrasound attenuation layers 73 are located between the electrodes 47a and the transmitting piezoelectric element 41 and between the electrode 47b and the receiving piezoelectric element 42.

In an ultrasound diagnostic apparatus of the present invention, a frequency of the ultrasound to be used is about 1 MHz to 10 MHz. Generally, an elastic material such as rubber has a high attenuation factor in the above frequency band, and thus can be used as an ultrasound attenuation material. Therefore, as this embodiment, when the respective conductive rubbers are located between the electrodes 47a and the transmitting piezoelectric element 41 and between the electrode 47b and the receiving piezoelectric element 42, predetermined electrical signals can be applied to the transmitting piezoelectric element 41 and the receiving piezoelectric element 42. In addition, the possibility that the ultrasound is propagated into the substrate 43 and directly received in the receiving piezoelectric element 42 can be lowered. As a result, since the strength of the ultrasound transmitted into the living body is increased, the detection sensitivity can be improved.

Note that, as shown in FIG. 27, it is required that the ultrasound attenuation layer 73 is divided between the transmitting piezoelectric element 41 and the receiving piezoelectric element 42. If the ultrasound attenuation layer 73 is not divided, the ultrasound from the transmitting piezoelectric element 41 easily propagates to the receiving piezoelectric element 42 through the ultrasound attenuation layer 73. This causes the reduction in the detection sensitivity.

Embodiment 18

Figure 28:
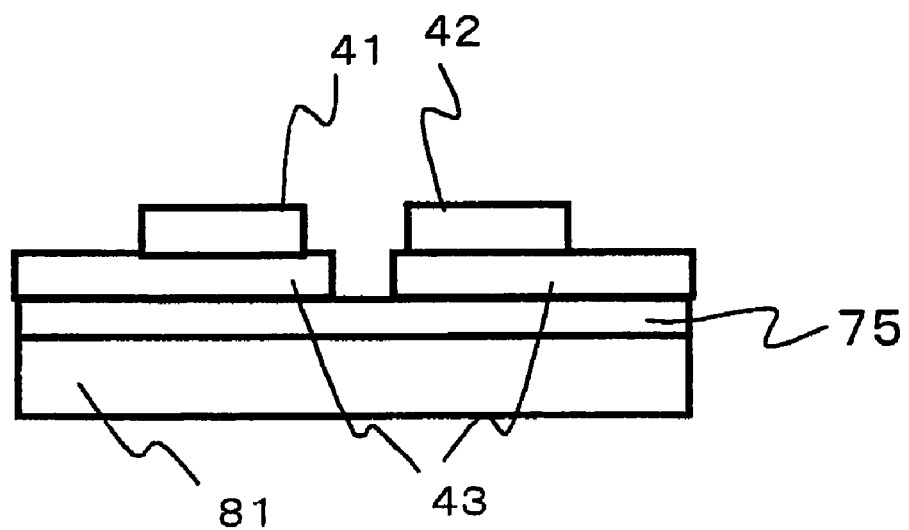
FIG. 28 shows one embodiment of the measurement unit (4)

One example of a pulse detecting device 1 as one embodiment of an ultrasound diagnostic apparatus of the present invention will be described using FIG. 28. FIG. 28 is a side view of a measurement unit 4 in the pulse detecting device of this embodiment. With respect to materials of the band, the processing unit, the clip, the piezoelectric elements, and the substrate, the same ones as in Embodiment 1 are used. The electrodes 45a, 45b, 46a, 46b, 60a, and 60b and the wirings 61 are omitted.

FIG. 28 shows a structure in which the transmitting piezoelectric element 41 and the receiving piezoelectric element 42 are located on the divided substrates 43 and the substrates 43 are fixed onto the support 81 through ultrasound attenuation layers 75.

As a material of the ultrasound attenuation layers 75, as described in Embodiment 3, epoxy resin containing tungsten powder, a porous material made from a material with porosity, conductive or insulating rubber described later, or the like is suitable.

Embodiment 19

Figure 29:
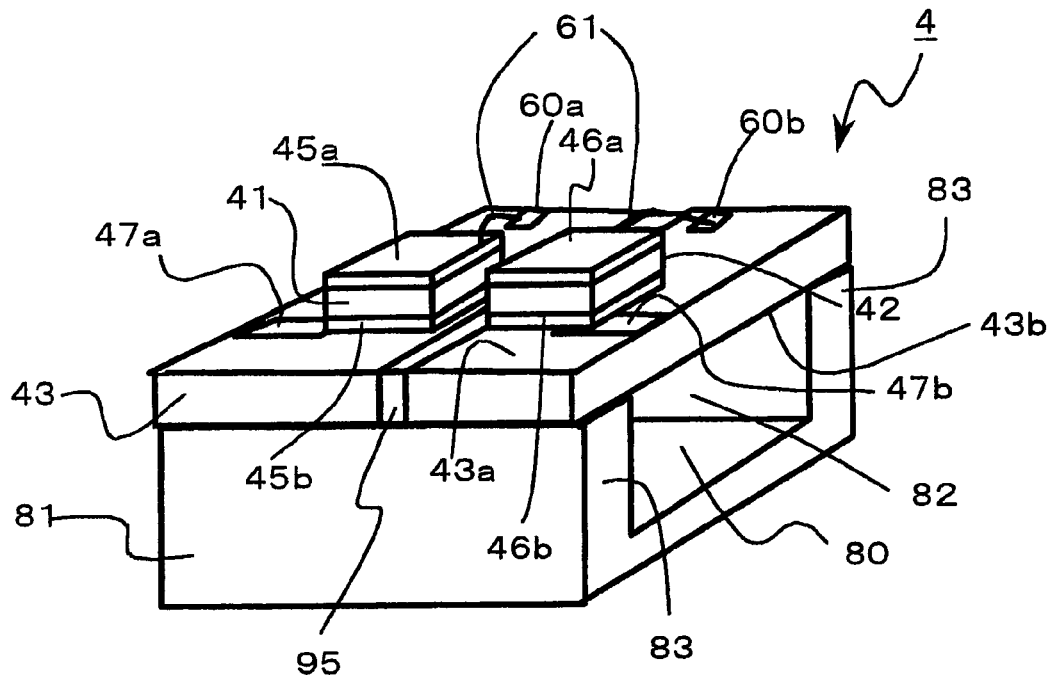
FIG. 29 shows one embodiment of the measurement unit (4)

One example of a pulse detecting device 1 as one embodiment of an ultrasound diagnostic apparatus of the present invention will be described using FIG. 29. FIG. 29 is a side view of a measurement unit 4 in the pulse detecting device of this embodiment. With respect to materials of the band, the processing unit, the clip, the piezoelectric elements, and the substrate, the same ones as in Embodiment 1 are used. The electrodes 45a, 45b, 46a, 46b, 60a, and 60b and the wirings 61 are omitted.

FIG. 29 shows a structure in which the substrates 43 are fixed onto the support 81 through ultrasound attenuation layers 75. By using the structure shown in FIG. 29, the possibility that the ultrasound is directly received in the receiving piezoelectric element 42 becomes lower. Therefore, the detection sensitivity can be improved.

Embodiment 20

Figure 30:
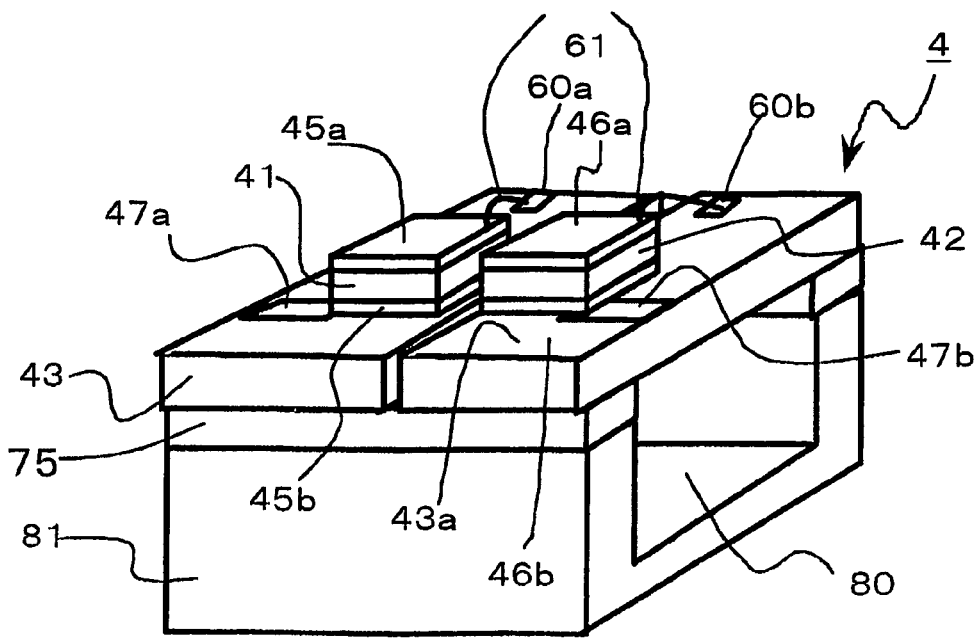
FIG. 30 shows one embodiment of the measurement unit (4)

One example of a pulse detecting device 1 as one embodiment of an ultrasound diagnostic apparatus of the present invention will be described using FIG. 30. FIG. 30 is a side view of a measurement unit 4 in the pulse detecting device of this embodiment. With respect to materials of the band, the processing unit, the clip, the piezoelectric elements, and the substrate, the same ones as in Embodiment 1 are used. The electrodes 45a, 45b, 46a, 46b, 60a, and 60b and the wirings 61 are omitted.

FIG. 30 is an explanatory view of a structure in which the substrate 43 is divided and an attenuation layers 95 is provided between the divided substrates 43 in the measurement unit 4 in which the support 81 with the concave portion 82 is provided.

When the measurement unit 4 is made to be in contact with the skin at the time of the pulse measurement or the like, a foreign matter such as a sweat or dust easily enters between the substrates 43. At this time, if the foreign matter such as a sweat or dust moves to the rear surface 43b opposite to one surface 43a of the substrate 43, the ultrasound generated by the transmitting piezoelectric element 41 directly propagates to the receiving piezoelectric element 42 easily through the foreign matter. This causes the reduction in the detection sensitivity.

Therefore, according to this embodiment, when the attenuation layer 95 is provided between the divided substrates 43, a foreign matter is unlikely to enter therebetween. Thus, the reduction in the detection sensitivity is prevented.

If acrylic system resin or epoxy based resin is used as a material of the attenuation layer 95, the ultrasound is propagated through such a resin. Thus, it is desirable that the attenuation layer 95 is made of a material such as silicon rubber, in which the ultrasound does not easily propagate.

Note that the pulse detecting device according to Embodiments 1 to 16 of the present invention can be also used for the ultrasound diagnostic apparatus. In addition, the ultrasound diagnostic apparatus according to Embodiments 17 to 20 can be also used for the pulse detecting device.

As described above, according to the pulse detecting device of the present invention, the transmitting piezoelectric element and the receiving piezoelectric element can be located on the substrate with high precision as designed. Thus, the pulse detecting device which resists fluctuations in the quality can be provided. In addition, the detection sensitivity of the pulse can be improved.

When the protrusions are provided in the substrate or the transmitting piezoelectric element and the receiving piezoelectric element, there are the following effects. That is, the ultrasound does not easily propagate to the substrate. The noise in the pulse detection is decreased. The transmitting strength and the receiving strength of the ultrasound to and from the living body can be improved. The detection sensitivity of the pulse is improved.

By the resin layer provided on the substrate of the pulse detecting device, a property of the contact surface of the substrate in contact with the living body can be suitably adjusted dependent on its use. In addition, the resin layer can be uniformly formed with a suitable thickness. Thus, the detection sensitivity of the pulse is further improved.

When the transmitting piezoelectric element and the receiving piezoelectric element are provided sandwiching the groove provided in the substrate, the ultrasound emitted from the transmitting piezoelectric element is not directly received in the receiving piezoelectric element. Thus, the noise can be decreased and the reliability of the pulse detecting device can be improved.

When the support substrate for supporting the transmitting piezoelectric element and the receiving piezoelectric element, which are located on the substrate, is provided, the strength against an external shock is improved and the leakage of the ultrasound can be prevented.

As described above, according to the pulse detecting device of the present invention, the transmitting piezoelectric element and the receiving piezoelectric element can be located on the transmitting and receiving substrate with high precision as designed. Thus, the pulse detecting device which resists fluctuations in the quality can be provided. In addition, the detection sensitivity of the pulse can be improved.

When the acoustic impedance of the transmitting and receiving substrate or the thickness thereof is controlled, the reflection of the ultrasound in the interface between the transmitting and receiving substrate and the living body can be reduced and the ultrasound can be propagated with high efficiency.

Since the structure is used such that the propagation direction of the ultrasound is set to be one direction, the ultrasound can be propagated with high efficiency.

By the resin layer provided in the transmitting and receiving substrate of the pulse detecting device, a property of the contact surface of the transmitting and receiving substrate in contact with the living body can be suitably adjusted depending on its use.

When the silicon based resin is used for the resin layer provided on the other surface, the adhesiveness between the transmitting and receiving substrate and the living body is improved. Therefore, the air layer in the interface between the transmitting and receiving substrate and the living body is decreased and thus the attenuation in an oscillation of the ultrasound can be suppressed.

When the transmitting piezoelectric element and the receiving piezoelectric element are provided sandwiching the groove provided in the transmitting and receiving substrate, the ultrasound emitted from the transmitting piezoelectric element is not directly received in the receiving piezoelectric element. Thus, the noise can be decreased and the reliability of the pulse detecting device can be improved.

The transmitting and receiving substrate is formed to slant one surface against the other surface. That is, one surface of the transmitting and receiving substrate is not in parallel with the other surface thereof and the transmitting and receiving substrate is formed with the taper shape. Therefore, the Doppler effect of the blood flow becomes larger and thus the detection sensitivity of the pulse can be improved.

When the support substrate for supporting the transmitting piezoelectric element and the receiving piezoelectric element, which are located on the substrate, is provided, the strength against an external shock is improved and the leakage of the ultrasound can be prevented.

By the display unit provided in the pulse detecting device, the pulse detection result can be grasped by the living body.

By providing the belt for putting the pulse detecting device, the pulse detecting device can be easily carried.

When the structure is used such that the transmitting piezoelectric element or the receiving piezoelectric element and the transmitting and receiving substrate are joined to each other by the metallic bond, the attenuation of the ultrasound in the junction interface becomes small and the ultrasound can be propagated with high efficiency.

As described above, according to the ultrasound diagnostic apparatus of the present invention, the piezoelectric elements are fixed onto the substrate only in the feed portions, the protrusions are provided on the substrate or the transmitting piezoelectric element and the receiving piezoelectric element to form the gaps as the ultrasound attenuation layers, or the ultrasound attenuation layers such as a porous material are provided. Thus, the structure is obtained such that the ultrasound do a substrate does not easily propagate from the transmitting piezoelectric element to the receiving piezoelectric element through the substrate. As a result, there is an effect that the ultrasound can be transmitted into the diagnostic portion with high efficiency and the detection sensitivity can be improved. Also, since the structure is used such that the piezoelectric elements are located on the substrate, the piezoelectric elements can be located with high precision, and thus this resists fluctuations in the quality. Further, the support for supporting the substrate is provided. Thus, the strength against an external shock and the ease of handling can be improved. Furthermore, the ultrasound attenuation layers are also provided between the support and the substrate. Thus, there is an effect that the ultrasound can be transmitted into the diagnostic portion with high efficiency and the detection sensitivity is improved.

Further, for example, the substrate may be divided to fix the divided substrates onto the support. Thus, there is an effect that the ultrasound can be transmitted into the diagnostic portion with higher efficiency and the detection sensitivity is further improved.

A member having an ultrasound attenuation characteristic, such as rubber, is provided between the divided substrates. Thus, since it is possible to prevent a foreign matter such as a sweat from entering or moving to the rear surface of the substrate to cause the noise, there is an effect that the stability in the detection is improved.

The transmitting piezoelectric element and the receiving piezoelectric element can be located on the substrate with high precision as designed. Thus, the ultrasound diagnostic apparatus which resists fluctuations in the quality can be provided.

What is claimed is:

1. An ultrasound diagnostic apparatus comprising:
    a transmitting piezoelectric element that transmits an ultrasound to a diagnostic portion of a body in response to an input drive signal;
    a receiving piezoelectric element that receives an echo produced by reflection of the ultrasound by the diagnostic portion of the body;
    a substrate having two spaced-apart non-contacting substrate sections, the transmitting piezoelectric element being disposed on and fixed to a surface of one substrate section and the receiving piezoelectric element being disposed on and fixed to a surface of the other substate section;
    a support member supporting the substrate, the support member having two spaced-apart side wall portions that have tops and bottoms, and a base portion interconnecting the bottoms of the two side wall portions, the two substrate sections being disposed on and supported by the tops of the two side wall portions so that the two substrate sections of the substrate jointly define with the two side wall portions and the base portion of the support member an enclosed gap that attenuates unwanted propagation of the transmitted ultrasound; and
    an information obtaining circuit that obtains information concerning the diagnostic portion of the body based on the transmitted ultrasound and the received echo.

2. An ultrasound diagnostic apparatus according to claim 1; wherein an ultrasound attenuating material is filled in the gap.

3. An ultrasound diagnostic apparatus according to claim 1; wherein the support member is made of one of ceramics, plastics or metal.

4. An ultrasound diagnostic apparatus according to claim 1; wherein a depth of the gap is equal to an ultrasound wavelength or more.

5. An ultrasound diagnostic apparatus according to claim 1; wherein a cross-sectional area of the gap is larger than a transmit plane of the transmitting piezoelectric element and a receive plane of the receiving piezoelectric element.

6. An ultrasound diagnostic apparatus according to claim 1; wherein the substrate has a thickness corresponding to substantially a quarter of a wavelength of the ultrasound generated by the transmitting piezoelectric element.

7. An ultrasound diagnostic apparatus according to claim 1; wherein the two substrate sections each have opposed top and bottom surfaces, the bottom surfaces of the two substrate sections being disposed on and supported by the top ends of the two side wall portions.

8. An ultrasound diagnostic apparatus according to claim 7; wherein the transmitting piezoelectric element and the receiving piezoelectric element are disposed on and fixed to the bottom surfaces of respective ones of the substrate sections.

9. An ultrasound diagnostic apparatus according to claim 8; further including a resin layer formed on the top surfaces of the two substrate sections.

10. An ultrasound diagnostic apparatus according to claim 8; wherein the top surfaces of the two substrate sections are inclined relative to one another less than 180 degrees.

11. An ultrasound diagnostic apparatus according to claim 1; wherein the two substrate sections are inclined relative to one another less than 180 degrees.

12. An ultrasound diagnostic apparatus comprising:

a transmitting piezoelectric element that transmits an ultrasound to a diagnostic portion of a body in response to an input drive signal;

a receiving piezoelectric element that receives an echo produced by reflection of the ultrasound by the diagnostic portion of the body;

a substrate having two spaced-apart non-contacting substrate sections, the transmitting piezoelectric element being disposed on and fixed to a surface of one substrate section and the receiving piezoelectric element being disposed on and fixed to a surface of the other substate section;

a support member supporting the substrate, the support member having a base portion and a plurality of projections projecting outwardly from the base portion, the two substrate sections being disposed on and supported by the projections so that the two substrate sections of the substrate jointly define with the projections and the base portion of the support member a gap that attenuates unwanted propagation of the transmitted ultrasound; and an information obtaining circuit that obtains information concerning the diagnostic portion of the body based on the transmitted ultrasound and the received echo.

13. An ultrasound diagnostic apparatus according to claim 12; wherein the plurality of projections comprises two side wall portions having bottoms connected to the base portion and tops that support the two substrate sections.

14. An ultrasound diagnostic apparatus according to claim 12; wherein the plurality of projections comprises columnar projections having bottoms connected to the base portion and tops that support the two substrate sections.

15. An ultrasound diagnostic apparatus according to claim 14; wherein the columnar projections are located at corner portions of the base portion.

16. An ultrasound diagnostic apparatus according to claim 12; wherein the plurality of projections comprises conical projections having bottoms connected to the base portion and tips that support the two substrate sections.

17. An ultrasound diagnostic apparatus according to claim 16; wherein the conical projections are located at corner portions of the base portion.

* * * * *